United States Patent
Paleari et al.

(10) Patent No.: US 9,945,791 B2
(45) Date of Patent: Apr. 17, 2018

(54) METHODS OF SPECTROSCOPIC ANALYSIS OF DIAMONDS AND APPARATUSES THEREOF

(71) Applicant: Università degli Studi di Milano-Bicocca, Milan (IT)

(72) Inventors: Alberto Maria Felice Paleari, Milan (IT); Roberto Lorenzi, Milan (IT); Andrea Zullino, Milan (IT)

(73) Assignee: UNIVERSITÀ DEGLI STUDI DI MILANO—BICOCCA, Milan (IT)

( * ) Notice: Subject to any disclaimer, the term of this patent is extended or adjusted under 35 U.S.C. 154(b) by 0 days.

(21) Appl. No.: 15/121,011

(22) PCT Filed: Feb. 28, 2014

(86) PCT No.: PCT/EP2014/053961
§ 371 (c)(1),
(2) Date: Aug. 23, 2016

(87) PCT Pub. No.: WO2015/127990
PCT Pub. Date: Sep. 3, 2015

(65) Prior Publication Data
US 2017/0010217 A1    Jan. 12, 2017

(51) Int. Cl.
*G01N 21/00*    (2006.01)
*G01N 21/87*    (2006.01)
(Continued)

(52) U.S. Cl.
CPC ............. *G01N 21/87* (2013.01); *G01N 21/65* (2013.01); *G01J 3/02* (2013.01); *G01N 21/68* (2013.01)

(58) Field of Classification Search
CPC ........ G01N 21/87; G01N 21/39; G01N 21/64; G01N 21/65; B07C 5/342
See application file for complete search history.

(56) References Cited

U.S. PATENT DOCUMENTS 5,883,389 A    3/1999  Spear et al.
6,377,340 B1 *  4/2002  Anthony ................ G01N 21/64
                                              250/330

FOREIGN PATENT DOCUMENTS

WO    03/023382 A1    3/2003

OTHER PUBLICATIONS

International Search Report and Written Opinion dated Dec. 2, 2014 from International Application No. PCT/EP2014/053961, pp. 1-4.
(Continued)

*Primary Examiner* — Abdullahi Nur
(74) *Attorney, Agent, or Firm* — MH2 Technology Law Group, LLP

(57) ABSTRACT

A method of spectroscopic analysis of a diamond for determining whether the diamond has been artificially treated to change its colour may include: generating light emission from a diamond upon optical excitation at a wavelength equal to or smaller than 680 nm; optically producing a dispersed light emission; detecting the dispersed light emission across a collected spectral region including emission wavelengths of from 670 nm to 735 nm; processing the output signals to produce a spectral intensity distribution as a function of emission wavelengths; analysing the spectral intensity distribution to determine the presence or absence of a spectral pattern including either an intensity peak at 681 nm or a combination of intensity peaks at respective wavelengths 705 nm and 725 nm; if a spectral pattern is present, establishing that the diamond has been treated; and if a spectral pattern is absent, establishing that the diamond has not been treated.

20 Claims, 13 Drawing Sheets

(51) Int. Cl.
 *G01N 21/65* (2006.01)
 *G01N 21/68* (2006.01)
 *G01J 3/02* (2006.01)

(56) References Cited

OTHER PUBLICATIONS

S.A. Solin, "Photoluminescence of natural type I and type IIb diamonds", Physics Letters. vol. 38A, No. 2, Jan. 17, 1972, pp. 101-102.
Thomas Hainschwang et al., "Luminescence spetroscopy and microscopy applied to study gem materials: a case study of C centre containing diamonds", Mineralogy and Petrology, vol. 107, No. 3, Feb. 13, 2013, pp. 393-413.
Christopher M. Breeding et al., "The 'Type' Classification System of Diamonds and Its Importance in Gemology", Gems & Gemology, vol. Summer 2009, Jun. 1, 2009, pp. 96-111.
Alan T. Collins, "The characterisation of point defects in diamond by luminescence spectroscopy", Diamond and Related Materials 1, 1992, pp. 457-469.
Hiroshi Kitawaki, "Gem Diamonds: Causes of Colors", New Diamond and Frontier Carbon Technology, vol. 17, No. 3, 2007, pp. 119-126.
Alan T. Collins, "Optical Centres Produced in Diamond by Radiation Damage", New Diamond and Frontier Carbon Technology, vol. 17, No. 2, 2007, pp. 47-61.

\* cited by examiner

METHODS OF SPECTROSCOPIC ANALYSIS OF DIAMONDS AND APPARATUSES THEREOF

CROSS REFERENCE TO RELATED APPLICATION(S)

No. PCT/EP2014/053961, filed on Feb. 28, 2014, in the Receiving Office ("RO/EP") of the European Patent Office ("EPO"), and published as International Publication No. WO 2015/127990 A1 on Sep. 3, 2015, the entire contents of which are incorporated herein by reference.

FIELD OF INVENTION

The present invention relates to a method for examining a gemstone, in particular aimed to the detection of artificial treatments of a diamond to change its colour. The present invention relates also to a spectroscopic apparatus of analysis of a gemstone.

RELATED ART

Diamonds for use as a gemstone are generally colourless and their quality is typically evaluated on clarity grade, colour grade, carat and cut. Colourless and transparent diamonds can be commercially highly valuable, but they are rarely found in nature. The first most commonly diamonds produced in nature are brown diamonds and yellow diamonds are the second most commonly found. As the amount of brown and/or yellow increases, the value of the diamond decreases. Nevertheless, gems with intense yellow colour or other colours, such as pink, green, blue, red and black are valued in the gem market primarily for the intensity and distribution of colour and because of their rarity. Strongly coloured quality gems are generally referred to fancy colour diamonds.

Artificial treatments to modify the diamond colour have been known and employed for many years. Along this widely performed practice, gemmological analysis techniques have been implemented with the aim of detecting whether a diamond has been artificially treated, such as by neutron or electron irradiation and/or by annealing processes.

A. T. Collins in "*Investigating artificially coloured diamonds*", published in Nature 273(1978), pages 654-655, studied the annealing behaviour at high temperatures of optical centres in irradiated diamonds, specifically of GR1 centre absorbing at 741 nm, H3 centre at 503 nm and the zero-phonon line at 595 nm. The author concluded that the absence of the 595-nm line does not unambiguously categorise a diamond as untreated and that further clues come from the relative strengths of the H3 and the H4 (at 496 nm) absorption bands.

A. T. Collins et al. in "*Spectroscopic studies of the H1b and H1c absorption lines in irradiated, annealed type-Ia diamonds*", published in J. Phys. C: Solid State Phys. 19 (1986) pages 3933-3944, studied the temperature dependence of the 595 nm (2.086 eV) absorption centre, together with the H1b and H1c defects, between 700 and 1000° C. in irradiated type-Ia diamonds. The author demonstrates a relationship between the 595 nm line and H1b (2024 nm) and H1c (1934 nm) zero-phonon absorption lines, showing that H1b and H1c centres are formed when all, or part, of the 2.086 eV centres is trapped at the A and B aggregate of nitrogen during the annealing process.

A. T. Collins in "*Optical Centres Produced in diamond by Radiation Damage*", published in New Diamond and Frontier Technology vol. 17 (2007), No. 2, pages 47-61, made a detailed review of the most important defects induced in diamond by electron irradiation and annealing processes, focusing on the absorption spectra of both type-I and type-II diamonds. In particular the author showed the relation between the vacancy production rates and the preexisting diamond defects and how these systems can be modified by HPHT processes and heat treatments. Depending on the impurities (for example boron or nitrogen atoms or aggregates) concentration, different defects can form in diamond lattice, such as GR1, ND1, H1b, H1c, H2, H3, H4, 5RL, 3H, N-V and 594 nm centres. All these optical centres are subjected to changes in concentration and creation rates depending on the diamond type, impurities and conditions of irradiation and annealing.

H. Kitawaki, in "*Gem diamonds: causes of colours*", published in New Diamond and Frontier Technology vol. 17 (2007), No. 3, pages 119-126, reviews the colour origin of diamonds and refers to electron or ion irradiation combined with annealing and to heat treatment under high-pressure and high-temperature (HPHT) as common treatment techniques. Photoluminescence analysis using a 514 nm or 488 nm argon ion laser is said to be effective to detect the HPHT process.

L. Tretiakova, in "*Spectroscopic methods for the identification of natural yellow gem-quality diamonds*", in Eur. J. Mineral. 21 (2009), pages 43-50, studied laser-induced photoluminescence spectroscopy of HPHT and irradiated and subsequent annealed yellow diamonds excited by a 514.5 nm laser. A 575-nm line was observed in the PL spectra on IaAB-type diamond, shifted to 572.2 nm when a green tint appears in yellow coloration. The 575 nm and 637 nm centres were observed to be connected and their intensity to depend on the dose and form of radiation, and apparently on the HPHT treatment conditions. A strong 535.8 nm line was present in HPHT diamonds and almost absent in annealed HPHT diamonds. This line was present also in a natural (i.e. untreated) green transmitter diamond. The author concluded that numerous clues to identifications can be detected by analysing diamonds with a wide range of spectroscopic techniques and that the study showed how the combination of spectroscopic methods including IR, optical absorption and PL spectroscopy could be successfully applied.

Defectiveness on atomic scale turns out to be different in natural diamonds with respect to diamonds exposed to ionizing radiation, regardless of the colour's similarity or even lack of difference of the two types of gemstones by visual inspection.

A. T. Collins, "*The characterisation of point defects in diamond by luminescence spectroscopy*", in Diamond and Related Materials 1 (1992), pages 457-469, considers photoluminescence and cathodoluminescence and discusses the defects responsible for the most significant luminescence band.

Absorption and luminescence spectra are reported in "*Colour changes produced in natural brown diamonds by high-pressure, high-temperature treatment*", published in Diamond and Related Materials 9 (2000), pages 113-122, by A. T. Collins et al., for natural brown diamonds before and after HPHT treatment at 1700-1800° C., and after HPHT treatment at 2025° C. Photoluminescence spectra produced by a 325-nm laser are shown and optical centres associated with nitrogen in the A form (nearest neighbour substitutional pairs) and B form (aggregates comprising four N atoms symmetrically surrounding a carbon vacancy) are discussed. Although A and B nitrogen are present in natural diamonds, results indicated that treatments create defect complexes with configuration that appear to be peculiar of artificially-processed samples.

U.S. Pat. No. 5,883,389 describes a method and apparatus for distinguishing natural diamonds from synthetic diamond by observing the ultraviolet (UV) photoluminescence. A diamond is illuminated with short wavelength UV radiation, i.e. 225 nm or less. An image of the photoluminescence patterns produced on the surface of the diamond is produced and studied by eye using magnifying means in the form of a microscope. A camera or a CCD image recorder is provided for later study or processing of the results.

Patent application WO 03/023382 relates to an apparatus for examining a diamond for detecting whether the diamond has been artificially irradiated or ion bombarded to change its colour or whether the diamond is a natural/synthetic doublet. Excitation by light is of from 500 to 740 nm, in particular at 633 nm (He—Ne laser), to excite luminescence from 680 nm to 800 nm, in particular the GR1 line at 741 nm. The diamond is placed below a confocal microscope having an objective lens and a confocal aperture and it is moved vertically. Above the microscope, a beam splitter, a laser for irradiating the diamond, a spectrometer and a processor. The confocal aperture prevents light from outside the focal region entering the spectrometer. The arrangement is such that the focal plane can be scanned through the diamond from the topmost point to the bottommost point.

The Applicant has observed that the use of a confocal microscope may relevantly increase the costs of an analysis apparatus. In addition, an accurate normalization procedure may be required to extract in-depth information on artificial treatments made to change the colour.

SUMMARY OF INVENTION

The present disclosure relates to a spectroscopic analysis method and apparatus for enabling the distinction of artificially irradiated coloured diamonds from natural coloured diamonds. In some preferred embodiments, the present method and apparatus allow in addition the discrimination of diamonds from different gemstones, i.e. the verification that the analysed gemstone is a diamond.

Examination of the change in colour and/or in crystal structure, the latter aimed for example to the elimination of lattice defects, which are achieved through artificial treatments is related to the possibility of identifying specific effects not occurring in natural gemstones. Those effects mainly concern sub-microscopic structural differences often invisible at the eye. Within the present description and claims, artificial treatments include artificial irradiation processes, such as ion, electron, neutron, and gamma-ray irradiation, and/or thermal treatments, such as high-temperature annealing.

The Applicant has observed that spectroscopic evidence of artificial treatments in yellow diamonds cannot be reliably obtained from the detection of the GR1 line at 741 nm.

The Applicant has found that by illuminating a diamond with an excitation wavelength lower than 681 nm, the occurrence of specific combinations of discrete photoluminescence features positioned at 681 nm, 705 nm, and at 725 nm indicates artificial treatments in the examined diamond, in particular if the gem under analysis is a yellow diamond.

In particular, the Applicant has found that a spectral pattern comprising either a spectral feature at 681 nm or a combination of spectral features at 705 nm and 725 nm is associated with an artificially treated diamond. With combination of spectral features at 705 and at 725 nm is meant the co-existence of both features at 705 and 725 nm.

The spectral pattern appearing in the emission spectrum and comprising at least one discrete spectral feature being either an intensity peak at 681 nm or the co-existence of two intensity peaks at respective wavelengths 705 nm and 725 nm is an indicator of artificial treatments of the diamond.

The Applicant has observed that the spectral pattern, and thus the discrete spectral features, are in general experimentally observed to be only few nm wide and therefore clearly distinguishable as intensity peaks in a intensity vs. wavelength spectrum, also when overlapped to broad spurious signals and/or other broad emissions not caused by treatments.

In some preferred embodiments, the spectral pattern is selected from the group consisting of: a spectral feature at 681 nm, two spectral features positioned at the respective wavelengths of 705 nm and at 725 nm, and three spectral features positioned at the respective wavelengths of 681 nm, 705 nm and 725 nm.

In some preferred embodiments, the excitation wavelength impinging on the gemstone is of from 350 nm to 680 nm, more preferably of from 350 nm to 675 nm. In some particularly preferred embodiments, the excitation wavelength is within the red spectral region of the visible light, more preferably at a wavelength of from 600 nm to 675 nm.

The spectral features of the spectral pattern, referred in the following also to as spectral indicators, are positioned, in the photoluminescence spectrum, at wavelengths within a relatively narrow wavelength region, which is of about 45 nm. The present method therefore allows the detection of whether the diamond has been artificially treated by measuring light emitted from the sample within a relatively narrow spectral region, making thereby possible the use of a light collection system of reduced complexity and cost.

The diamond Raman peak at 1332 cm$^{-1}$ univocally identifies the analysed gemstone as single-crystal diamond. The Applicant has noted that this Raman signal lies within the spectral region exhibiting the spectral pattern if the light excitation wavelength is chosen in the range of from 600 nm to 675 nm. For example, the Raman line falls at 691 nm for excitation wavelength of 633 nm.

The Applicant has observed that the present disclosure can be applied for the analysis of brown-coloured, orange-coloured, and of yellow-coloured diamonds, including any tone or saturation of these colours. In the following description this category of coloured diamonds will be referred, for brevity, to as yellow diamonds.

In most cases of interest, spectral indicators have been found to be weakly dependent on temperature and it has been observed that their peak intensity is relatively high in irradiated and treated diamonds. Although measurement of spectral response at cryogenic temperature, for example at liquid nitrogen temperature, may increase detection sensitivity, the method according to the present disclosure does not necessarily require cooling of the sample or the use of cooled detectors to enhance sensitivity.

Due to the relatively narrow spectral range to be measured for the detection of the indicators, employment of complex optics, such as wavelength-adjustable light dispersion elements, e.g. a rotating diffraction grating, is not necessary.

Since spectral indicators are not related to the determination of a in-depth concentration profile of defects, no expensive confocal optical system is required to collect photoluminescence intensity profile. Therefore, in accordance with some preferred embodiments, the present method allows the use of a relatively simple and compact detection apparatus that can be produced at low cost.

Consistently with the present disclosure, a method of spectroscopic analysis of a diamond for determining whether the diamond has been artificially treated to change its colour is provided, the method comprising:

generating light emission from a diamond upon optical excitation at an excitation wavelength equal to or smaller than 680 nm;

optically producing a dispersed light emission;

detecting the dispersed light emission across a collected spectral region by means of a photodetector device to electrically generate output signals, wherein the collected spectral region comprises emission wavelengths of from 670 nm to 735 nm;

processing the output signals to produce a spectral intensity distribution as a function of emission wavelengths;

analysing the spectral intensity distribution to determine the presence or absence of a spectral pattern comprising either an intensity peak at 681 nm or a combination of intensity peaks at respective wavelengths 705 nm and 725 nm;

if, as a result of analysing, a spectral pattern is determined to be present, establishing that the diamond has been artificially treated to change its colour, and if, as a result of analysing, a spectral pattern is determined to be absent, establishing that the diamond has not been treated to change its colour.

Preferably, the excitation wavelength is equal to or smaller than 675 nm. In some embodiments, the excitation wavelength is of from 350 nm to 675 nm.

Preferably, the collected spectral region comprises emission wavelengths of from 670 nm to 750 nm, more preferably collected spectral region comprises emission wavelengths of from 640 nm to 750 nm. In some preferred embodiments, the collected spectral region of excited emission for analysis of the spectral pattern comprises a wavelength range of from 650 nm to 800 nm. In a particular embodiment, the collected spectral range of excited emission is of from 650 to 950 nm.

In some preferred embodiments, analysing the spectral intensity distribution and establishing that the diamond is treated or untreated is performed automatically by a processing module configured to receive and process the spectral intensity distribution and to generate processed data.

Preferably, the method further comprises, after establishing that the diamond has been artificially treated, providing an output indicating that the diamond has been artificially treated.

In some embodiments, the method further comprises, after establishing that the diamond is untreated, providing an output indicating that the diamond is untreated.

Preferably, providing an output indicating that the diamond has been artificially treated or is untreated is performed automatically.

According to some embodiments, the processing module runs in one or more processors which can be installed in a user terminal operatively connectable to the processing circuit of the photodetector device or being a separated control unit, preferably located within the spectroscopic apparatus, connected to the processing circuit.

In some embodiments, the processing module is executed by a processor, which is embedded in or connected to a user terminal with a display screen and an input unit for interaction with a user. The processing module is operatively connected to a rendering module, preferably running on the processor, having graphic processing for rendering a bidimensional graph of the spectral intensity distribution on the display screen.

In an embodiment, providing an output indicating that the diamond has been artificially treated comprises visualising a message on the display screen (e.g. through the rendering module).

In a further embodiment, providing an output indicating that the diamond has been artificially treated comprising activating a sound signal, wherein activation is triggered by the processing module to produce an audio sound from an audio unit of a user terminal embedding the processing module or from an electronic alarm unit installed on the spectroscopic apparatus and logically connected to the processing module.

In some embodiments, the method further comprises, after analysing the spectral intensity distribution and before establishing if the diamond is untreated or has been artificially treated, visualising on a display screen the spectral intensity distribution.

In an embodiment, the method further comprising, after analysing the spectral intensity distribution and before establishing that the diamond is untreated or artificially treated, visualising on a display screen the spectral intensity distribution and, if the spectral pattern is determined to be present, displaying an indication of the position of the spectral pattern on the display screen, wherein analysing the spectral intensity distribution is performed automatically and establishing that the diamond is treated or untreated is performed by a user based on the displayed indication.

Preferably, generating light emission from a diamond comprises irradiating a diamond with a primary optical beam at an excitation wavelength to generate excited light emission in the form of a secondary optical beam.

Preferably, the primary light beam is a monochromatic light beam.

Preferably, optically producing a dispersed light emission comprises focussing the secondary optical beam onto a slit to produce an image of light emission, and spectrally dispersing the secondary light beam to spatially separate the light emission imaged by the slit into wavelengths across the collected spectral region.

In some preferred embodiments, analysing the spectral intensity distribution to determine the presence or absence of a spectral pattern comprises:

analysing the spectral intensity distribution to determine the presence or absence of an intensity peak at 681 nm;

if, as a result of analysing, an intensity peak at 681 nm is determined to be present, determining that the spectral pattern is present;

if, as a result of analysing, an intensity peak at 681 nm is determined to be absent, analysing the spectral intensity distribution to determine the presence or absence of an intensity peak at 705 nm;

if, as a result of analysing, an intensity peak at 705 nm is determined to be absent, determining that the spectral pattern is absent;

if an intensity peak at 705 nm is determined to be present, analysing the spectral intensity distribution to determine the presence or absence of an intensity peak at 725 nm;

if an intensity peak at 725 nm are determined to be present, determining that the spectral pattern is present, if an intensity peak at 725 nm is determined to be absent, determining that the spectral pattern is absent.

Preferably, the diamond is a yellow diamond.

According to some embodiments consistent with the present disclosure, a method of identifying a gemstone as a diamond and, if the gemstone is identified as diamond, of determining whether the diamond has been artificially treated is provided, the method comprising:

generating light emission from a diamond upon optical excitation at an excitation wavelength equal to or smaller than 680 nm;

optically producing a dispersed light emission;

detecting the dispersed light emission across a collected spectral region by means of a photodetector device to electrically generate output signals, wherein the collected spectral region comprises emission wavelengths of from 670 nm to 735 nm;

processing the output signals to produce a spectral intensity distribution as a function of emission wavelengths;

analysing the spectral intensity distribution to determine the presence or absence of a Raman peak at a wavelength corresponding to a wavenumber shift between the excitation wavelength and the scattered wavelength of 1332.5 $cm^{-1}$;

if, as a result of analysing, a Raman peak is determined to be absent, establishing that the gemstone is not a diamond and providing an output indicating that the gemstone is not a diamond;

if, as a result of analysing, a Raman peak is determined to be present, establishing that the gemstone is a diamond and proceed by analysing the spectral intensity distribution to determine the presence or absence of a spectral pattern comprising either an intensity peak at 681 nm or a combination of intensity peaks at respective wavelengths 705 nm and 725 nm;

if, as a result of analysing, a spectral pattern is determined to be present, establishing that the diamond has been artificially treated to change its colour, if, as a result of analysing, a spectral pattern is determined to be absent, establishing that the diamond has not been treated to change its colour, and providing an output indicating that the diamond has been artificially treated.

Preferably, excitation wavelength is of from 600 nm to 675 nm.

Preferably, the method of identifying a gemstone as a diamond and, if the gemstone is identified as diamond, of determining whether the diamond has been artificially treated is performed automatically.

In accordance with some embodiments, the method comprises:

before analysing the spectral intensity distribution to determine the presence or absence of a spectral pattern, selecting a diamond colour from two colour groups: a first colour group of yellow, orange and brown and a second colour group of blue-green or black;

if the diamond colour is selected to be the first group of colour, proceeding with analysing the spectral intensity distribution to determine the presence or absence of the spectral pattern and establishing if the diamond has been artificially treated;

if the diamond colour is selected to be the second group of colour, analysing the spectral intensity distribution to determine the presence or absence of a GR1 spectral feature at 741 nm;

if, as a result of analysing, a GR1 spectral feature is determined to be present, establishing that the diamond in the second colour group has been artificially treated to change its colour and providing an output that the diamond has been artificially treated; and if, as a result of analysing, a GR1 spectral feature is determined to be absent, establishing that the diamond has not been treated to change its colour.

In some preferred embodiments, the steps subsequent selecting a diamond colour are performed automatically.

Consistently with the present disclosure, a spectroscopic apparatus is provided, which comprises:

a source emitting a primary beam at an excitation wavelength equal to or smaller than 680 nm to be directed onto a diamond to generate light emission from the diamond;

a first optical focussing system arranged to focus the light emission onto a slit to produce an image of light emission;

a spectrally dispersing device arranged to spatially separate the light emission imaged by the slit into wavelengths, the spectrally dispersing device being configured to produce a spatially dispersed light emission;

a photodetector device arranged to collect the dispersed light emission across a collected spectral region and to electrically generate output signals, wherein the collected spectral region comprises a wavelength region of spatially dispersed light emission of from 670 nm to 735 nm;

a processing circuit configured to receive the output signals and to process them to produce a spectral intensity distribution as a function of emission wavelength across the collected wavelength region, and a processor operatively connected to the processing circuit comprising a processing module configured to:

analyse the spectral intensity distribution to determine the presence or absence of a spectral pattern comprising either an intensity peak at 681 nm or a combination of intensity peaks at respective wavelengths 705 nm and 725 nm;

establish that the diamond has been artificially treated to change its colour if, as a result of analysing, a spectral pattern is determined to be present, and establish that the diamond has not been treated to change its colour if, as a result of analysing, a spectral pattern is determined to be absent.

Preferably, the processing module is further configured to trigger the provision of an output indicating that the diamond has been artificially treated, after establishing that the diamond has been artificially treated.

In some embodiments, the processor comprises a rendering module operatively connected to the processing module for rendering a graph of the spectral intensity distribution on a display screen operatively connected to the processor.

In some embodiments, the spectrally dispersing device is a reflection diffraction grating or a transmission diffraction grating.

Preferably, the apparatus further comprises a second optical focussing system arranged to collect the dispersed light emission from the spectrally dispersing device and to direct a focussed dispersed light emission onto the photodetector device.

BRIEF DESCRIPTION OF THE DRAWINGS

The present invention will now be described in more detail hereinafter with reference to the accompanying drawings, in which some, but not all embodiments of the invention are shown. Drawings illustrating the embodiments are not-to-scale schematic representations.

For the purpose of the present description and of the appended claims, except where otherwise indicated, all numbers expressing amounts, quantities, percentages, and so forth, are to be understood as being modified in all instances by the term "about". In most embodiments, wavelength values of the spectral indicators, namely 681 nm, 705 nm and 725 nm, are to be understood as mean value within a range of ±5 nm, the range of values reflecting a typical experimental uncertainty in the wavelength position of the intensity peaks.

Also, all ranges include the maximum and minimum points disclosed and include any intermediate ranges therein, which may or may not be specifically enumerated herein.

Figure 1A:
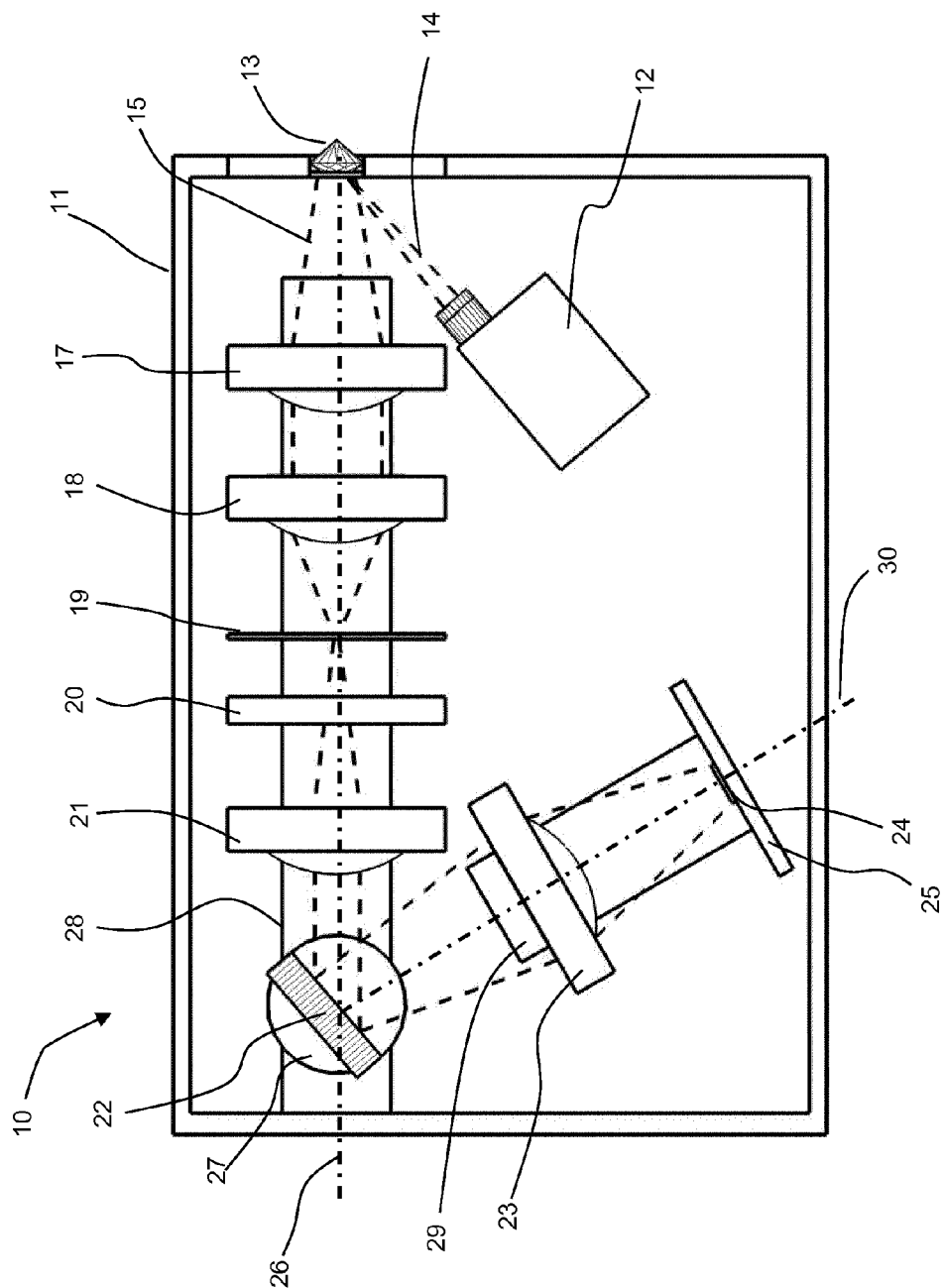

FIG. 1a is a block diagram of an analysis spectroscopic apparatus (top view) in accordance with an embodiment consistent with the present disclosure.

Figure 1B:
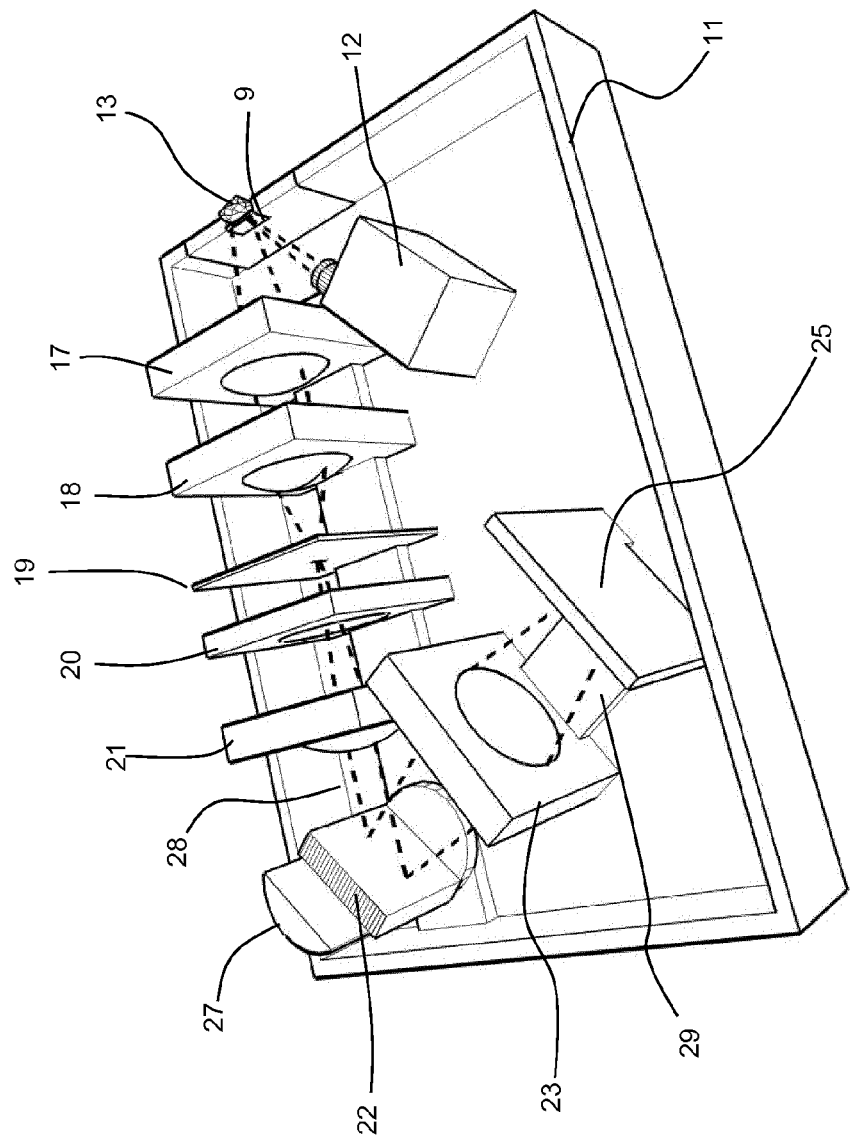

FIG. 1b is a schematic perspective view of the analysis spectroscopic apparatus of FIG. 1a.

Figure 2:
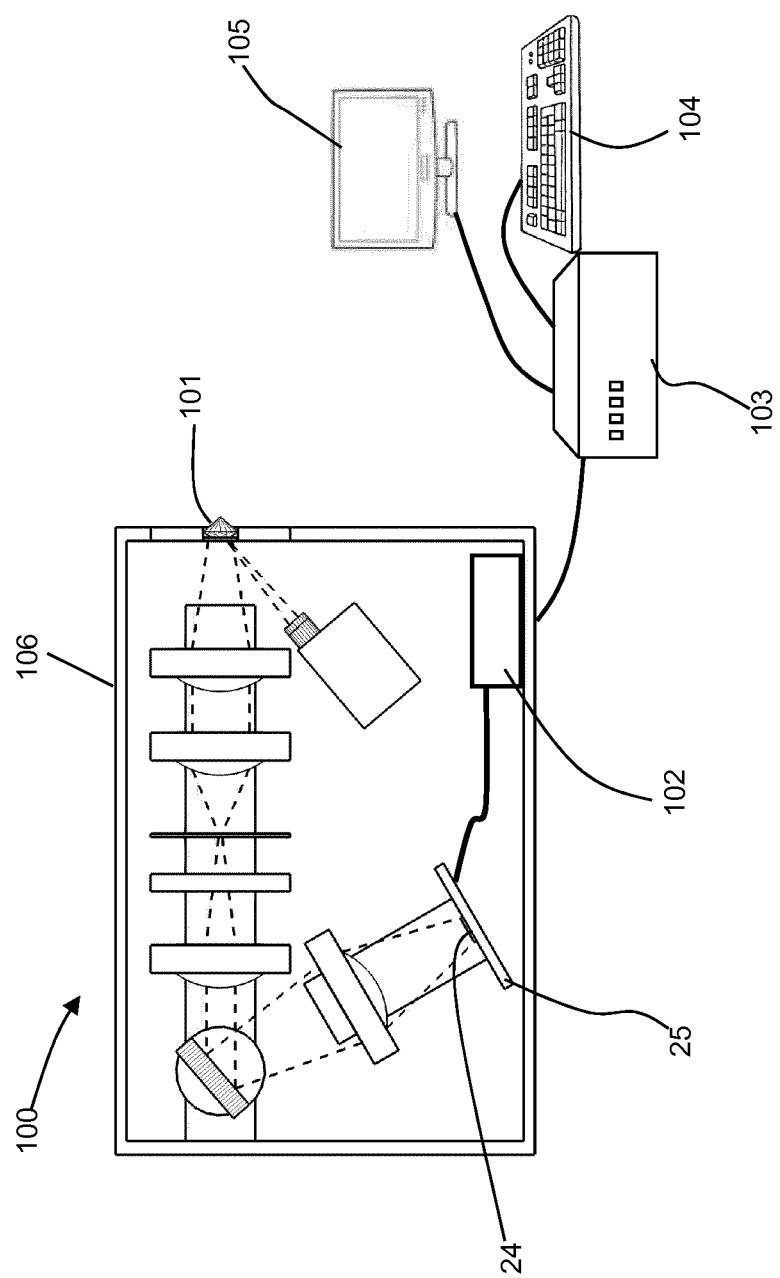

FIG. 2 is a block diagram of an analysis spectroscopic apparatus in accordance with another embodiment consistent with the present disclosure.

Figure 3:
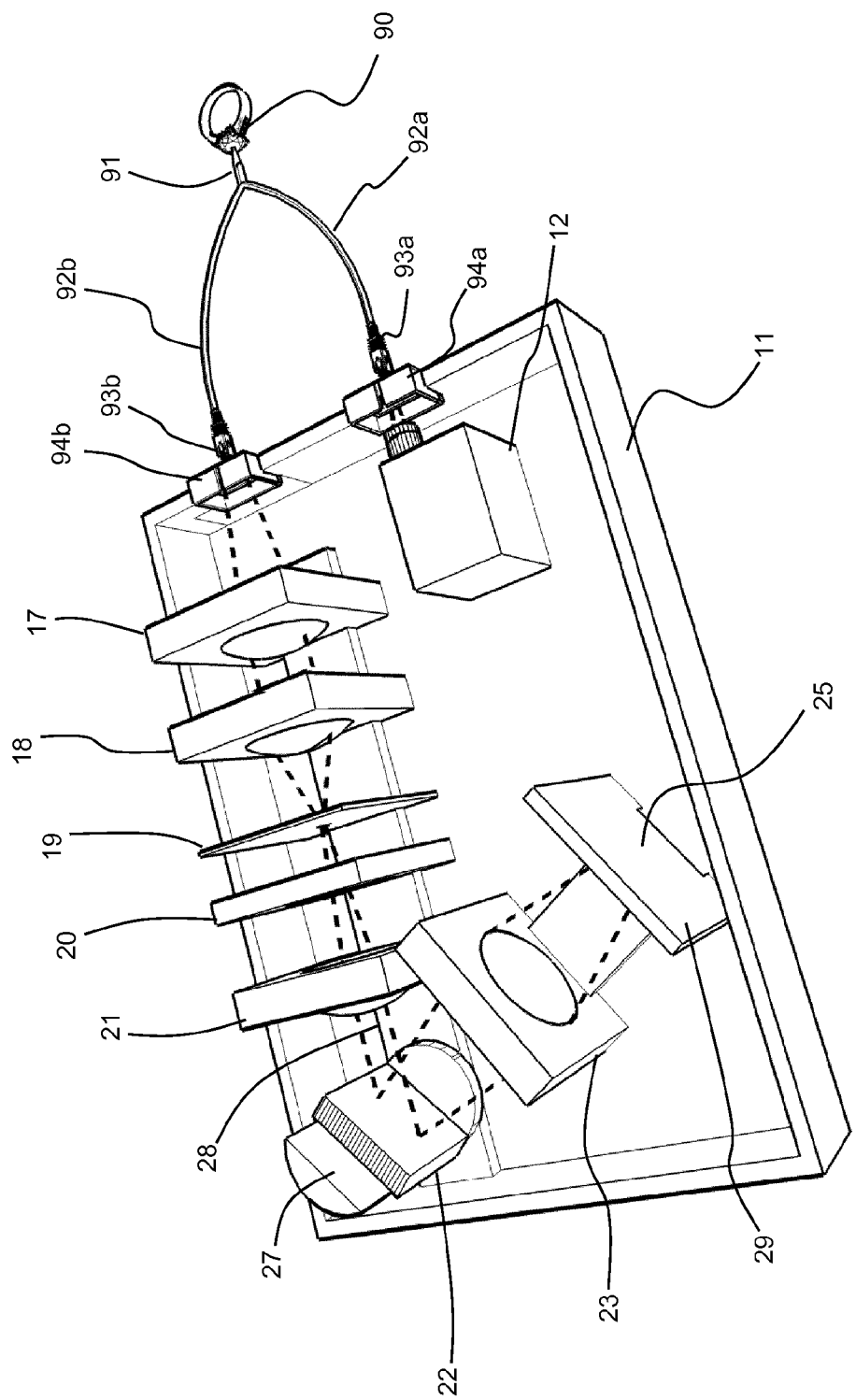
Figure 4:
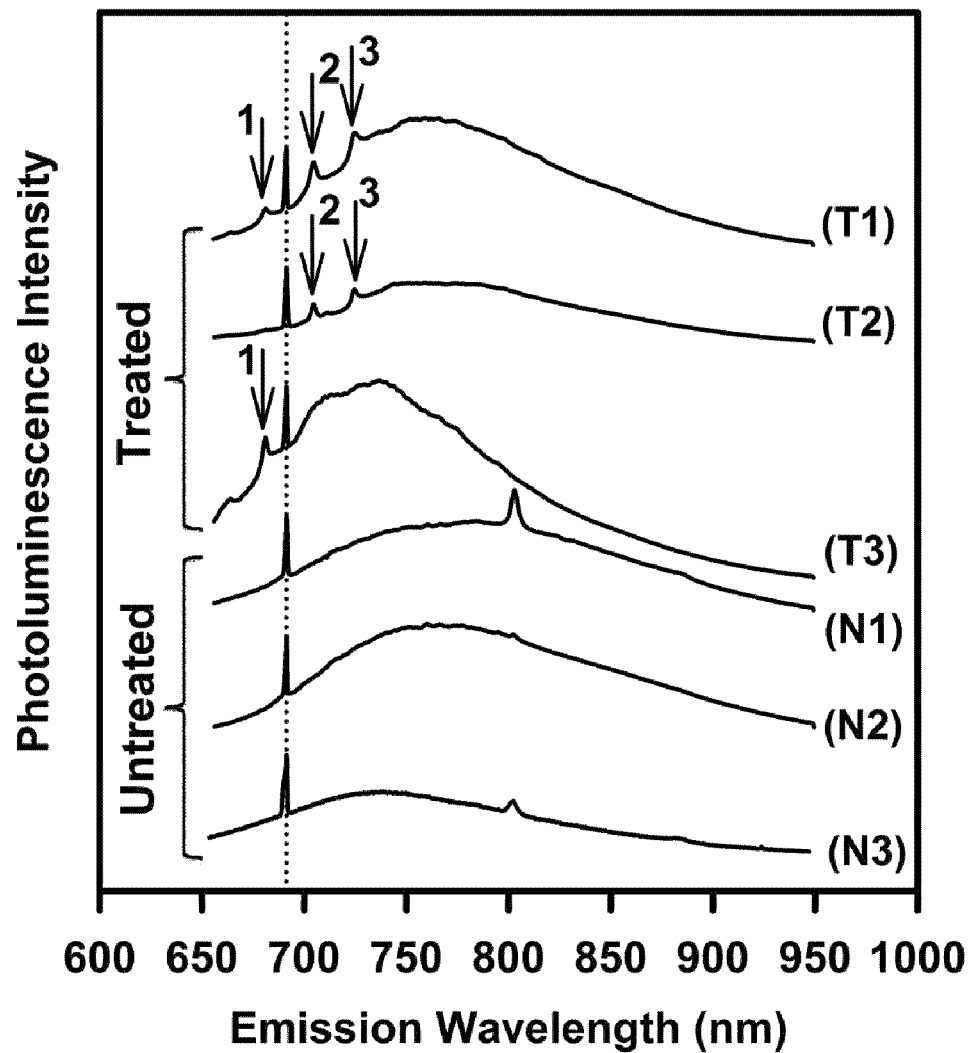

FIG. 3 is a block diagram of an analysis spectroscopic apparatus in accordance with still another embodiment consistent with the present disclosure FIG. 4 reports exemplary photoluminescence spectra for an excitation wavelength of 633 nm, from yellow diamonds, namely artificially treated yellow diamonds indicated with T1, T2, and T3 and natural, i.e. untreated, yellow diamonds indicated with N1, N2, and N3.

Figure 5:
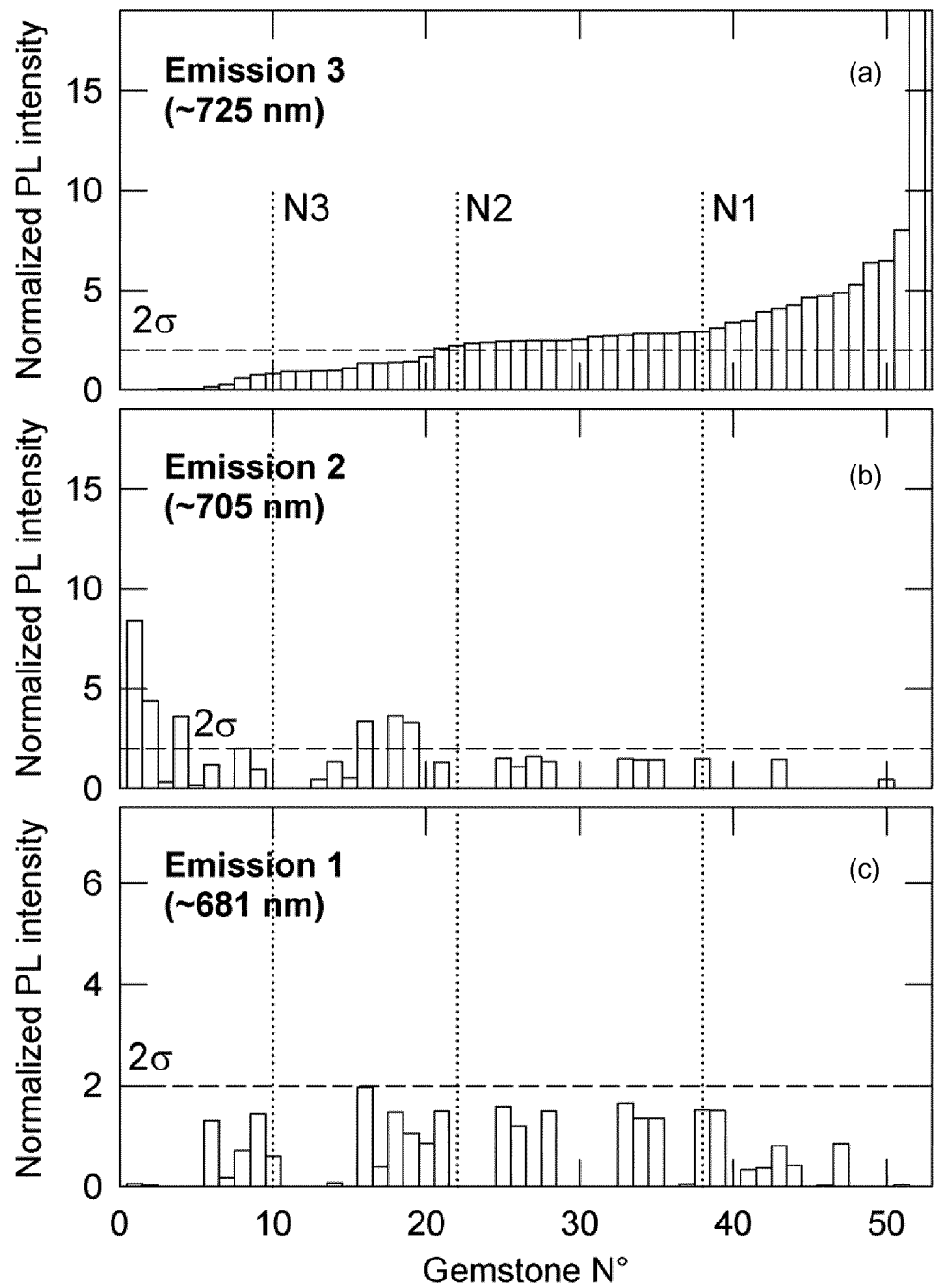

FIG. 5 is a histogram constructed by plotting three charts (a)-(c) reporting individual values of normalised photoluminescence intensity measured for the spectral features on naturally coloured yellow diamonds.

Figure 6:
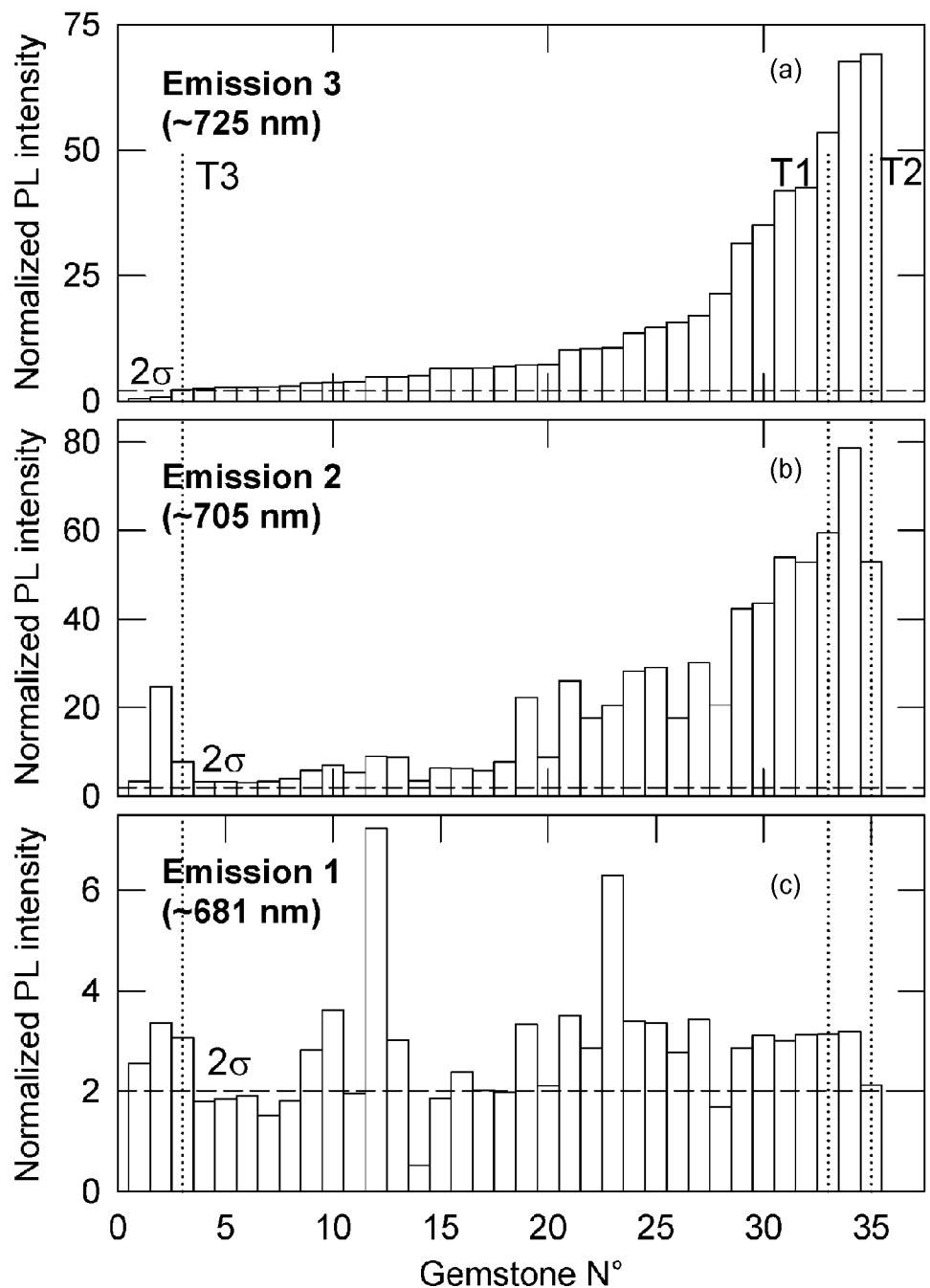

FIG. 6 is a histogram constructed by plotting three charts (a)-(c) reporting individual values of normalised photoluminescence intensity measured for the spectral features on artificially coloured yellow diamonds.

Figure 7:
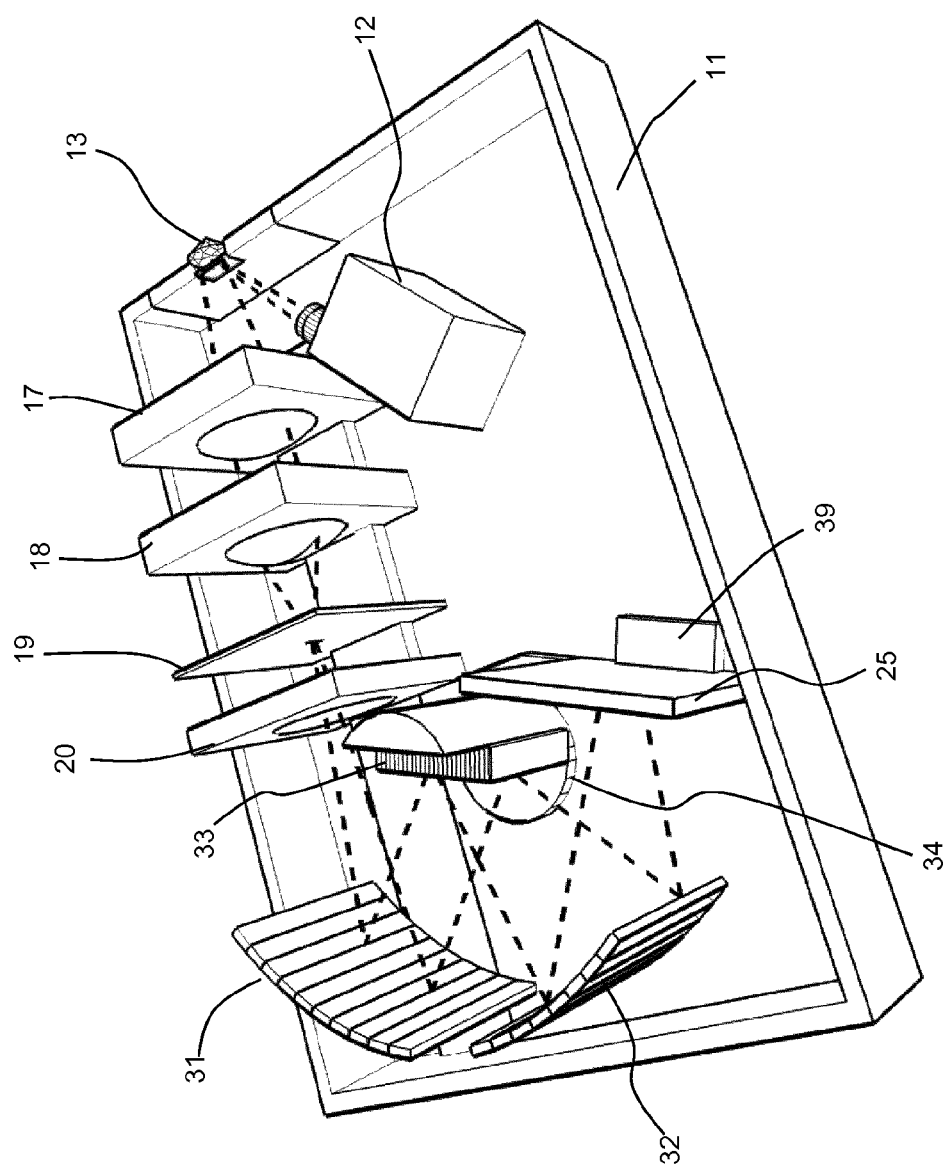

FIG. 7 is a block diagram of an analysis spectroscopic apparatus in accordance with another embodiment consistent with the present disclosure.

Figure 8:
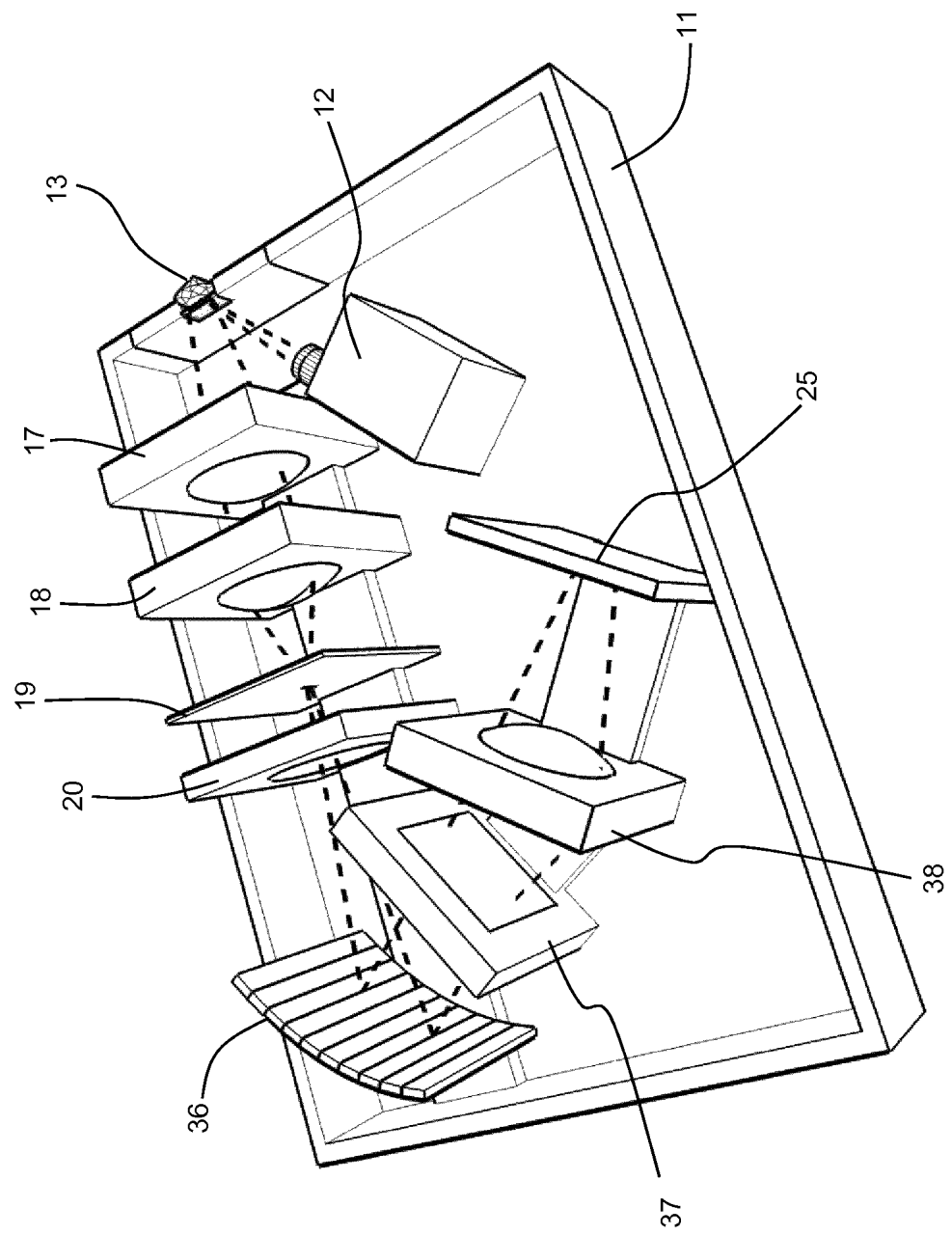
Figure 9:
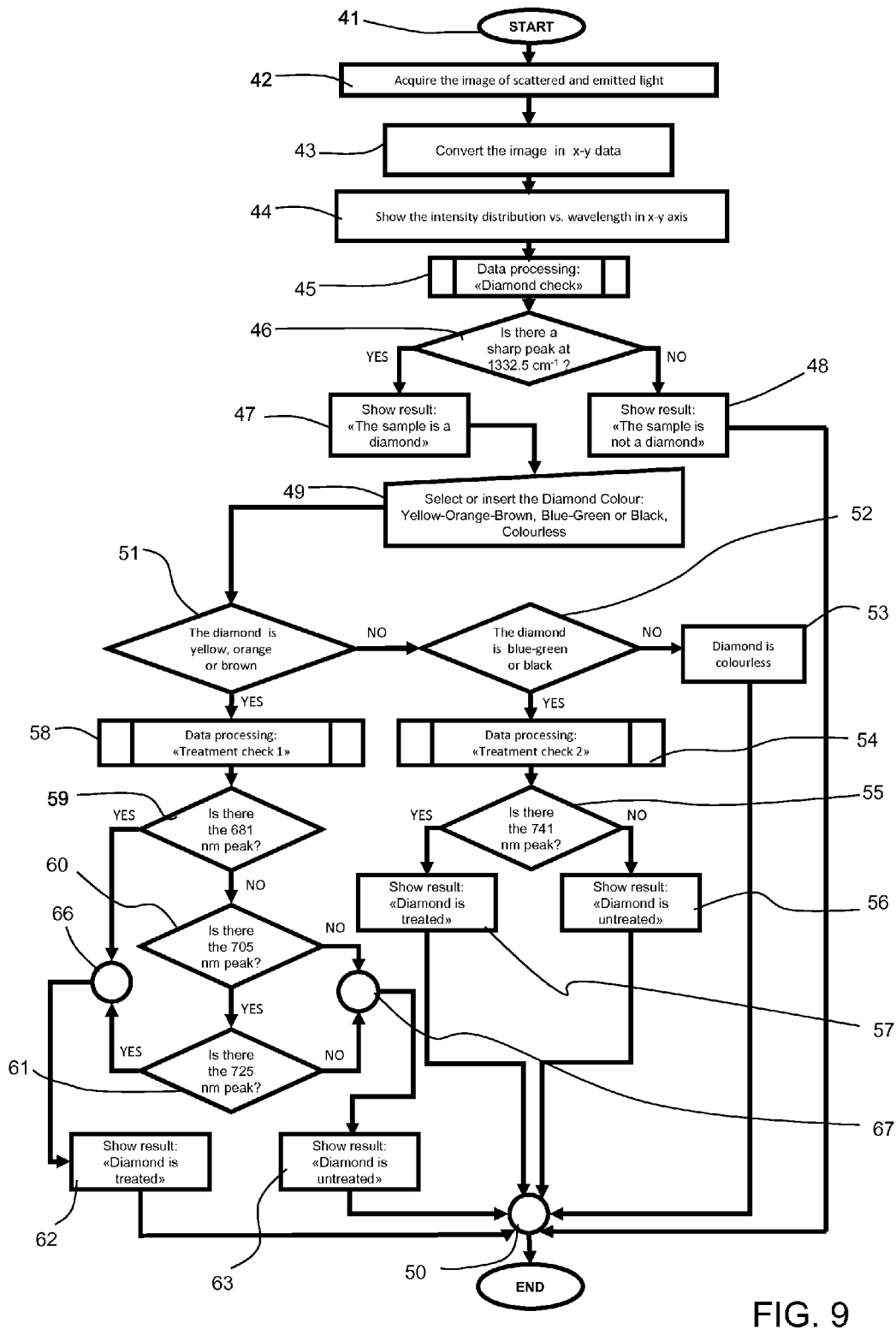

FIG. 8 is a block diagram of an analysis spectroscopic apparatus in accordance with a further embodiment consistent with the present disclosure FIG. 9 is a flowchart of a method of detection of artificially generated colour in a gemstone, in accordance with an embodiment consistent with the present disclosure.

Figure 10:
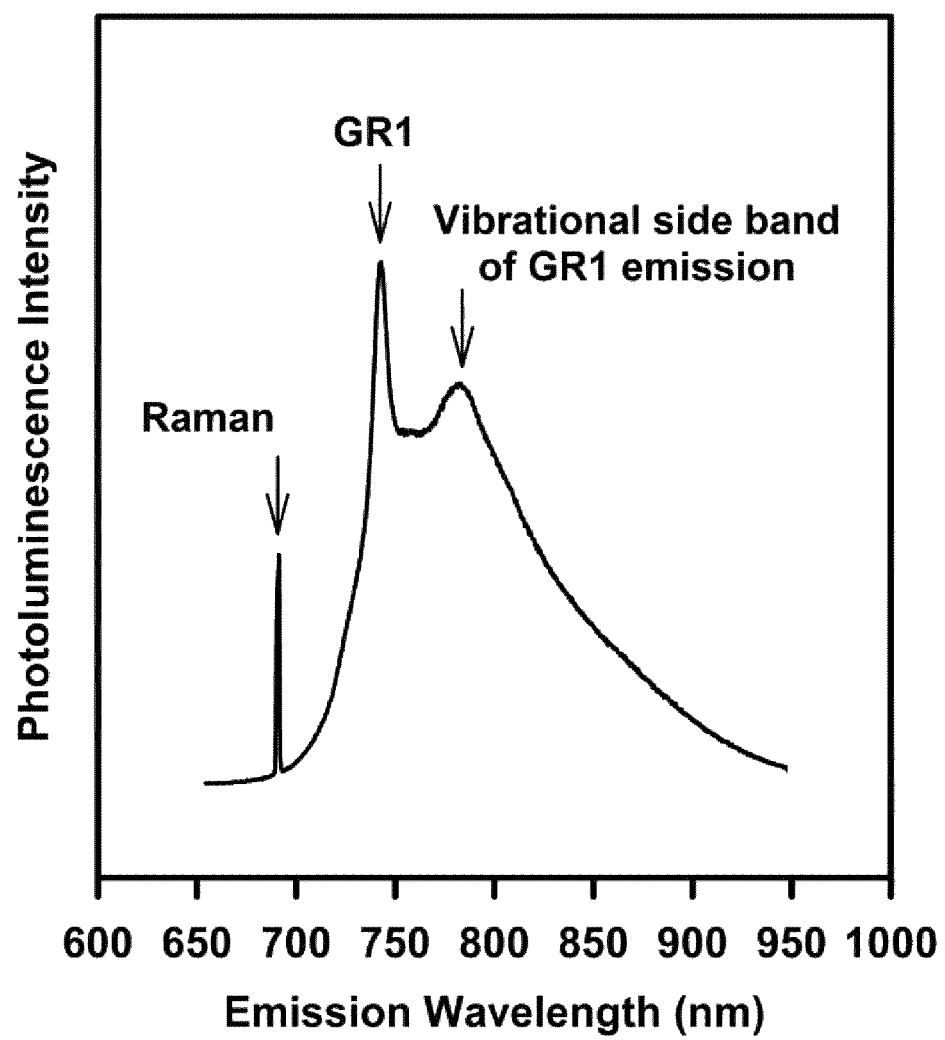

FIG. 10 is a plot of an exemplary photoluminescence spectrum, collected by exciting at 633 nm from an artificially treated light-blue diamond.

Figure 11:
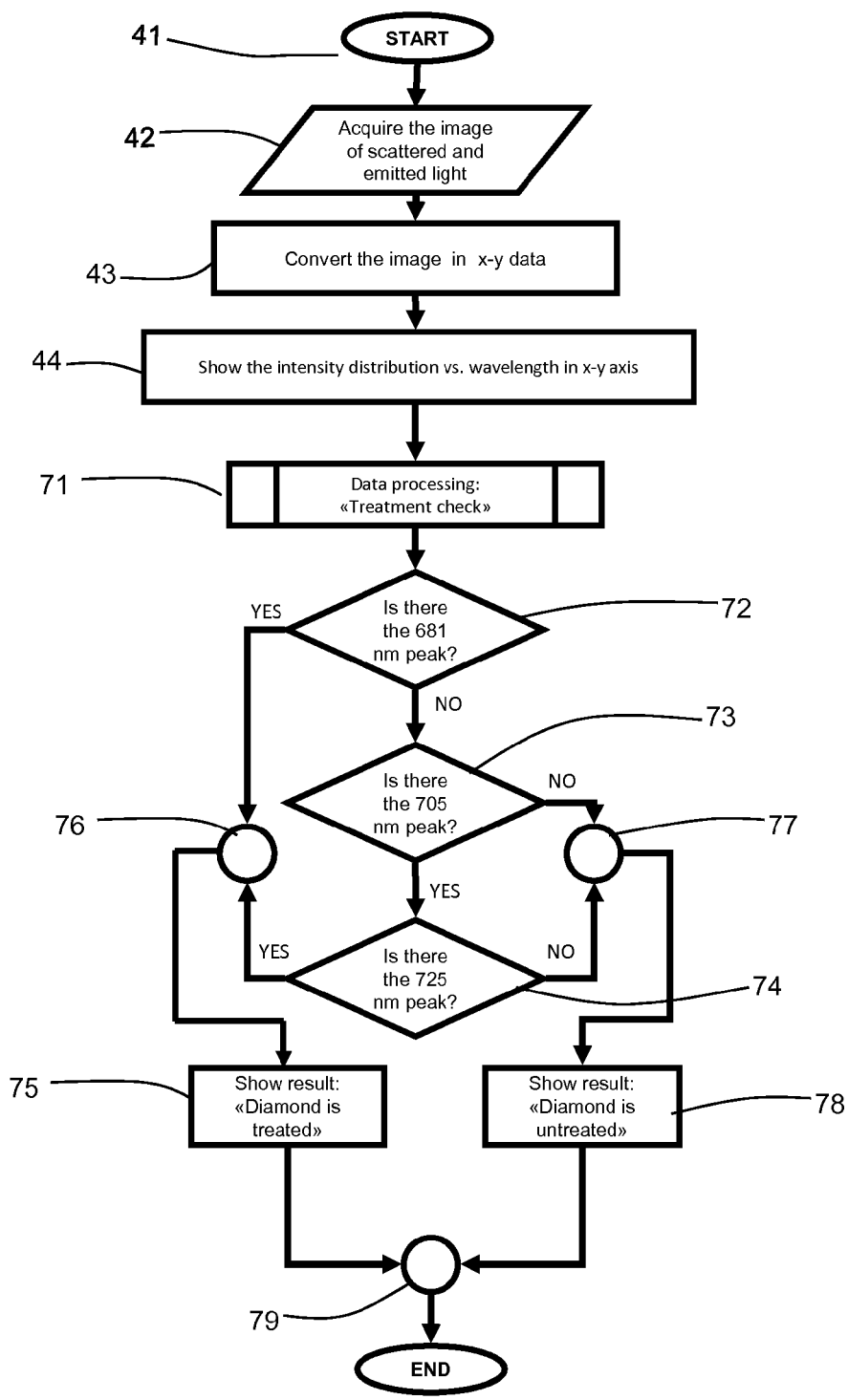

FIG. 11 is a flowchart of a method of detection of artificially generated colour in a diamond, in accordance with another embodiment consistent with the present disclosure.

Figure 12:
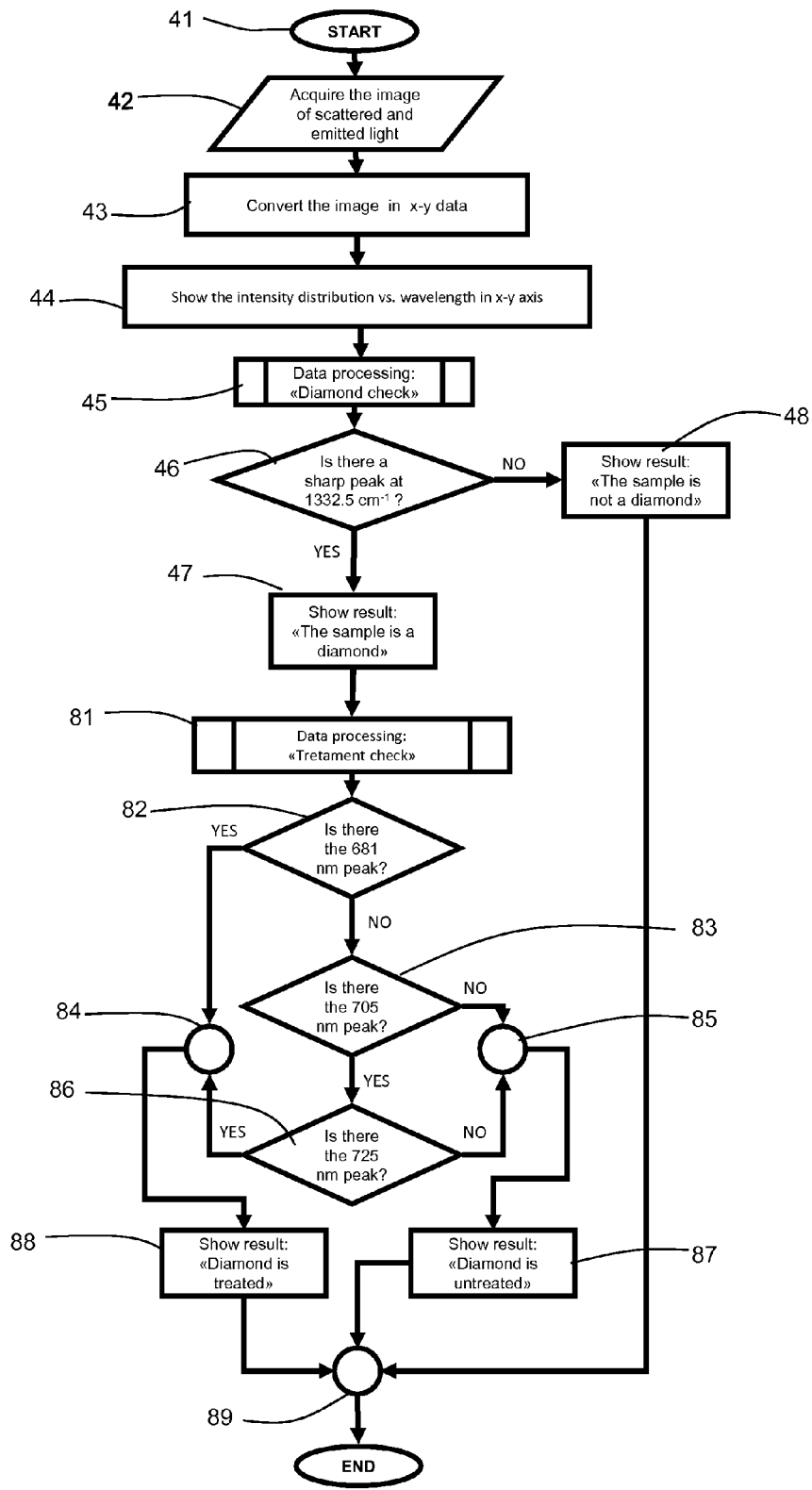

FIG. 12 is a flowchart of a method of detection of artificially generated colour in a gemstone, in accordance with still a further embodiment consistent with the present disclosure.

DETAILED DESCRIPTION

FIGS. 1a and 1b are a top view and a perspective view, respectively, of an apparatus for spectroscopic analysis of a gemstone according to an embodiment consistent with the present disclosure. An apparatus 10 comprises a light source 12 configured to emit a primary light beam 14 and arranged so as to direct the beam onto a sample 13, which is a gemstone and in particular a diamond. The light source is configured to emit a light beam at a wavelength equal to or smaller than about 680 nm. Preferably, light source is configured to emit a monochromatic light beam at a wavelength of from 350 nm to 680 nm, more preferably of from 350 nm to 675 nm. More preferably, the light source is configured to emit monochromatic light in the visible red wavelength spectrum, at a wavelength of from 600 to 675 nm.

In an embodiment, the light source is a light emitting diode (LED) emitting monochromatic light at a wavelength of 635 nm. In a further embodiment, the light source is a laser device emitting at 633 nm. The diamond is exposed to the light beam that generates optically excited emission and scattered light at room temperature from the sample. The emitted and scattered light, which will be referred also to as secondary light beam (indicated in FIG. 1a with referral number 15), is collected by a first focussing optical system arranged to receive the excited emission and having two focussing lenses 17 and 18, the second lens 18 being positioned downstream the first lens with respect to the sample. In the embodiment of FIGS. 1a-1b, the first focussing optical system consists of first and second focussing lenses. In another embodiment, the first focussing optical system may be formed by a single focussing lens, for example a biconvex lens. Light passed through the focussing optical system is focussed onto a slit 19 to form an image of the light emission from the sample. The width of the slit are preferably selected to obtain the width of the slit image on the sensor of the same order of a single pixel of the detector device described in the following.

Preferably, a wavelength-selective filter 20 is arranged to receive the secondary light beam, coming from the slit 19, for filtering out possible light originating from the primary beam elastically scattered at the excitation wavelength within the sample, or originating from scattering centres caused by surface roughness of the sample. In some embodiments, the wavelength-selective filter 20 is an optical band pass filter or a high pass filter. In an embodiment, the filter is a high pass filter with cut-off wavelength larger than the excitation wavelength. For example, excitation wavelength is 633 nm and a high pass filter with cut-off wavelength of 640 nm is selected.

After having passed though slit 19, and preferably being filtered to select a wavelength region, the secondary light beam is collimated by a collimating lens 21 on a light dispersion element 22 configured to distribute in space the secondary light beam as a function of wavelength. In the present embodiment, the light dispersion element 22 is a reflection diffraction grating. In a conventional way, the light dispersion element is mounted on a mounting structure 27 for stably holding the light dispersion element in a suitable position to receive the incoming light beam.

The dispersed beam is collected by a second focussing optical system 23 which focuses it on a photodetector device 24. The second light focusing system 23 of the present embodiment is a focussing lens. The photodetector device is electrically connected to a signal processing circuit 25 configured to process the output photocurrent signals and to generate x-y data, which are preferably suitable to be viewed in an image graphically visualised on a display screen. In some embodiments, the x-y data is the spectral distribution of the signal intensity as a function of wavelength.

Passive optical elements for focalisation, collimation and dispersion of the secondary light beam are preferably arranged along a first optical axis 26 in the optical path of the secondary light beam emitted from the sample. The reflection diffraction grating directs the received secondary beam on the photodetector that is arranged to receive the dispersed secondary light beam along a second optical axis 30.

In the usual ways, the optical elements arranged along the first optical axis 26 can be held in place by a first supporting structure 28, while the optical elements arranged along the second optical axis 30 can be held in place by a second supporting structure 29.

In some embodiments, the photodetector device is a CCD (Charge Coupled Device) light sensor or a CMOS (Complementary Metal Oxide Semiconductor) light sensor. In some embodiments, the photodetector device is configured to detect a wavelength spectrum covering visible and near-IR light. The spectroscopic analysis apparatus of FIGS. 1a and 1b is housed in a housing 11 shaped as a box having an open top, which can be closed by a lid (not shown in the figures). Mounting tools are employed to hold the diamond in place during measurements. For example, a slot 9 is formed on a side wall of box 11 (visible in FIG. 1b) for insertion of sample 13.

The x-y data of the spectrum, i.e. intensity vs. wavelength, exiting the processing circuit 25 are entered in a processing module (not shown in FIGS. 1A and 1B) for spectral analysis configured to implement the method of spectral analysis and, in some embodiments, configured to receive input data from a user, process the input data and the spectrum data (i.e., the x-y data), and to generate processed data.

FIG. 2 schematically illustrates an exemplary arrangement for the spectral analysis and the verification of the presence of an artificial treatment in the gemstone. An apparatus 100 for spectroscopic analysis of a gemstone 101 comprises opto-electronic devices and optical components to produce and optically analyse an emission light spectrum from the gemstone according to some embodiments herein disclosed. For example, the optical configuration of the apparatus can be the same as that described with reference to FIGS. 1A and 1B. In particular, a photodetector 24 is connected to a processing circuit 25 configured to process the output photocurrent signals and to generate x-y data describing the spectral distribution of the intensity in the detected image as a function of wavelength. The processing circuit 25 is logically connected to a processing module configured to: analyse the spectral intensity distribution to determine the presence or absence of spectral pattern indicative of artificial treatment and to establish that the diamond has been artificially treated to change its colour if, as a result of analysing, the spectral pattern is determined to be present. Preferably, the processing module is configured to provide an output indicating that the diamond has been artificially treated after establishing that the spectral pattern is present.

In the embodiment shown in FIG. 2, the processing module is a software program running on a processor 102 connected to the processing circuit 25. The software may include, for example, routines, programs, objects, components, and data structures that perform particular functions. The processor 102 is housed in housing 106, which houses the apparatus for spectroscopic analysis and it is connected to a computer 103, such as PC, external from apparatus 100. In the usual ways, the housing 106 can be provided with a PC access port for connection with an external computer (103).

In a conventional way, the processing module for spectral analysis is connected to a rendering module, which can run on processor 102 and includes graphic processing for rendering a bidimensional spectrum for interaction with the user through a display screen 105 of the computer. The computer can be provided with an input unit, e.g. a keyboard 104.

In another embodiment (not shown in FIG. 2), the processing module is embedded in a personal computer (PC), logically connected to the processing circuit 25, or more generally it can be executed on a user terminal, such as a PC, tablet or smartphone.

FIG. 3 is a block diagram (perspective view) of an apparatus for spectroscopic analysis of a gemstone according to a further embodiment consistent with the present disclosure. Same referral numbers employed in FIGS. 1a and 1b indicate same or like elements. The apparatus of FIG. 3 differs from the embodiment of FIGS. 1a and 1b mainly in that sample excitation and collection of scattered/emitted light is achieved by means of an optical fibre system. In the present embodiment, a first optical fibre 92a has a first end optically coupled with the output of the light source 12. An optical connector 93a terminates the first end of the optical fibre 92a and is connected with a lateral wall of the housing 11 through a first optical flange 94a. The optical fibre 92a transmits the exciting light to a sample 90, i.e. a gemstone, from the light source. The scattered/emitted light coming from the sample is optically coupled with a second optical fibre 92b for transmission to the entrance of the first focusing system. An optical connector 93b terminates a first end of the second fibre 92b and is connected with the lateral wall of the housing through a second optical flange 94b. Second ends of the first and second optical fibres 92a and 92b are spliced with one another in a common termination portion 91, which is a length of an optical fibre connected, e.g. by splicing, with the joined second ends of fibres 92a and 92b. The common terminating portion 91 is placed in front and in proximity of the irradiating surface of the sample. In some embodiments, the present configuration enables an easy and efficient coupling of the device to the probed sample for small size gems either loose or set on jewels. In another embodiment, a bundle of optical fibres, for example a bundle of 4, 6, 18 or of 24 fibres are used instead of a single optical fibre for coupling light onto and from the sample.

FIG. 4 is a plot of photoluminescence intensity (arbitrary units) versus wavelength of excited emission with excitation wavelength of 633 nm from several samples detected at a wavelength region of from 650 nm to 950 nm. Primary beam was emitted from a laser having optical power of about 30 mW. Spectra were collected at room temperature from three artificially irradiated yellow diamonds labelled with T1, T2, and T3, respectively, and from three natural, i.e. untreated, yellow diamonds labelled with N1, N2, and N3. At least a narrow spectral feature at 681 nm (labelled with number 1 in the figure) is observed in treated samples T1 and T3. Sample T2 presents a peak at 705 nm and a peak at 725 nm, which are labelled with numbers 2 and 3, respectively, in FIG. 4. The spectrum of sample T3 shows only peak 1, whereas sample T1 exhibits all three peaks 1, 2 and 3.

None of spectral features 1, 2 and 3 is present in the spectra collected from natural yellow-coloured diamonds N1, N2 and N3. A sharp narrow intensity peak at about 691 nm is present in all spectra of FIG. 4, at the spectral position corresponding to the Raman line single-crystal diamond at wavenumber of 1332 $cm^{-1}$. Only to improve readability, a dotted line passing through the Raman peaks is traced in FIG. 4. The Raman peak is caused by the Raman mode associated to intrinsic vibrations of the diamond crystal structure, known to be observed in all diamonds, independently of their treatment, colour, shape, and geological origin of the gemstone.

Photoluminescence peaks labelled 1, 2 and 3 are observed to be superimposed to other spectral contributions comprising a broad fluorescence, which is often observed also in natural diamonds, as shown in the spectra of samples N1 to N3.

The Applicant observed that either at least a spectral feature at 681 nm or at least a combination of spectral features at 705 nm and 725 nm is systematically present in artificially treated yellow diamonds, whereas the spectral features at 681 or the co-existence of the 705 and 725 nm features are absent in natural, i.e. untreated diamonds. The presence of all three spectral features has been observed to be present only in artificially treated yellow diamonds.

In particular, the Applicant carried out an investigation on the occurrence of the spectral features 1, 2 and 3 in a statistically relevant set of diamonds, comprising coloured diamonds of different commercial origin.

FIG. 5 is a histogram constructed by plotting three charts reporting individual values of normalised photoluminescence intensity experimentally measured at 681 nm (chart (c)), 705 nm (chart (b)) and at 725 nm (chart (a)) on 53 samples of naturally coloured yellow diamonds. The abscissa of the charts reports the sample number. Photoluminescence spectra for the investigated diamonds were collected and fitted in the same spectral region comprising the wavelengths of the spectral pattern, namely 650-950 nm, to evaluate the relative intensity of the spectral indicators. In particular, each intensity peak at the specific wavelengths was normalized to the noise amplitude estimated as standard deviation a of the mean value of the intensity in a signal free spectral range, after subtraction of the underlying broad fluorescence. Horizontal dashed line drawn in each chart as a constant value of photoluminescence intensity indicates, for each intensity peak at the specific wavelengths, the value of $2\sigma$, where $\sigma$ is the standard deviation of noise in the spectra. Peaks with intensity larger than $2\sigma$ at wavelengths usually within ±5 nm of the wavelength value labelled in the figure, were considered to represent a positive determination of a spectral feature. Vertical dotted lines indicates the measurements on samples N1, N2 and N3 discussed with reference to FIG. 4.

With reference to chart (c) of FIG. 5, none of the analysed naturally coloured diamonds shows a spectral feature greater than $2\sigma$ at 681 nm. From chart (b), a few samples exhibit a spectral feature at about 705 nm, i.e. a photoluminescence peak exceeding $2\sigma$, while some samples show a pronounced spectral feature at about 725 nm. However, photoluminescence spectra of none of the gemstones exhibit both the intensity peak at 705 nm and the peak at 725 nm. Therefore, the spectral pattern indicative of artificial treatment is absent in any of the examined naturally coloured diamonds.

FIG. 6 is a histogram constructed by plotting three charts reporting individual values of normalised photoluminescence intensity experimentally measured at 681 nm (chart (c)), 705 nm (chart (b)) and at 725 nm (chart (a)) on 35 samples of yellow diamonds artificially treated by irradiation and annealing, in which occurrence of an artificial treatment was demonstrated by known and independent fingerprints, including infrared electronic transitions at around 5000 $cm^{-1}$ for the detection of H1b and H1c optical centres or optical absorption at 595 nm for the detection of 595 centre or at H3 (503 nm) and H4 (496 nm) centres. Vertical dotted lines indicates the measurements on the samples T1, T2 and T3 discussed with reference to FIG. 4. Horizontal dashed line drawn in each chart as a constant value of photoluminescence intensity indicates, for each intensity peak at the specific wavelengths, the value of $2\sigma$. Occurrence of one of the three peaks 1, 2 and 3 with an intensity larger than $2\sigma$ above the noise was defined to be a positive determination of a spectral feature.

In FIG. 6, for example, it can be observed that gemstones from Nos. 3 to 35 show both a peak at 705 nm and a peak at 725 nm, whereas samples Nos. 1 and 2 show a peak at 681 nm, but not the combination of peaks at 705 and 725 nm. In general, spectra of all examined diamonds show one of the following spectral patterns: a peak at 681 nm, coexisting peaks at 705 and 725 nm, and all three peaks.

Results shown in FIGS. 5 and 6 demonstrate a correlation between the detection of peaks within the wavelength range comprising the spectral pattern (labelled 1, 2, and 3, respectively, in the figures) and treatments carried out on the gemstones. The occurrence of the 681 nm peak and simultaneously, or alternatively, the coexisting occurrence of the peaks at 705 nm and 725 nm (both with intensity more than $2\sigma$ above the noise) can be taken as a sufficient condition to distinguish treated diamonds from natural diamonds. Based on this facts, the luminescence peak at 681 nm and the pair of peaks at 705 nm and 725 nm, if simultaneously observed, are considered to constitute the spectral indicators of artificial treatments in a diamond.

FIG. 7 is a block diagram (perspective view) of a spectroscopic analysis apparatus according to a further embodiment consistent with the present disclosure. Same referral numbers employed in FIGS. 1a and 1b indicate same or like elements. The apparatus of FIG. 6 differs from the embodiment of FIGS. 1a and 1b mainly in the collimation of the secondary optical beam onto the light dispersing element and in the second optical focussing system for directing the light-dispersed secondary beam onto the photodetector device. In particular, the secondary light beam, which has passed through wavelength-selective filter 20, impinges on a first parabolic mirror 31 arranged to receive the secondary light beam and to direct the received beam onto a light dispersion element 33, preferably a reflection diffraction grating. Dispersed light reflected from light dispersion element 33 impinges on a second parabolic mirror 32, arranged to receive the dispersed light and to direct the dispersed light on photodetector device 24 (not visible in the figure, since it is hidden behind the processing circuitry 25). Light dispersion element 33 and photodetector device 24 can be mounted on a respective supporting structures 34 and 39 to ease optical alignment.

FIG. 8 is a block diagram (perspective view) of a spectroscopic analysis apparatus according to a another embodiment consistent with the present disclosure. Same referral numbers employed in FIGS. 1a and 1b indicate same or like elements. The apparatus of FIG. 8 differs from the embodiment of FIGS. 1a and 1b in the optical components downstream the wavelength-selective filter 20. The apparatus of FIG. 8 comprises a parabolic mirror 36 positioned to receive the filtered light beam from filter 20 and to direct it to a light dispersion element 37, which is a transmission diffraction grating. The dispersed light, which is transmitted by the diffraction grating 37, is focussed onto photodetector 24 (not visible in the figure) by a focussing lens 38.

It is to be understood that, although not shown in FIGS. 3, 7, and 8, the processing circuit 25 is connected, in at least during operation, to a processing module, which can be installed in a processor housed in housing 10 or installed in a PC or other suitable user terminals, such as tablets or smartphones.

FIG. 9 is a flow chart of a method of analysis of a gemstone and in particular of detection of artificially generated colour in a diamond, in accordance with an embodiment consistent with the present disclosure. The method starts (41) with the acquisition of the secondary light beam emitted from a gemstone, assumed to be a diamond, by means of a photodetector device (step 42), following excitation with a primary beam at a wavelength selected within a range from 600 nm to 675 nm. For the generation and acquisition of the secondary light beam, a spectroscopic analysis apparatus such as those described with reference to FIGS. 1a-1b, 2, 3, 7 and 8 can be employed. Electronic output signals containing the information on the scattered and emitted light are output from photodetector device, such as a CCD sensor. Following acquisition of the secondary light beam by the photodetector device, output signals are processed in a manner per se known by converting them to produce x-y data of spectral intensity distribution (step 43), which are suitable for viewing in an image graphically visualised on a display. The x-y data are input data for a photoluminescence spectrum having as y-data the intensity of the detected beam and as x-data the wavelengths within a collected spectral region. Preferably, the collected spectral region comprises a wavelength region of from 670 nm to 750 nm, more preferably of from 650 nm to 800 nm. In some embodiments, the collected spectral region is of from 650 nm to 950 nm. The spectrum can be visualised as a graph of the type shown in FIG. 4 (optional step 44). Conversion of the raw data from the photodetector device is performed by conventional hardware and software for image processing, which can be comprised in a processing circuitry connected to the photodetector device, such as processing circuit 25 of embodiments of FIGS. 1a-1b, 2-3, 7 or 8, or being part of the photodetector device.

The x-y data of the spectrum, i.e. intensity vs. wavelength, are entered in a processing module for spectral analysis configured to receive input data from a user, process the input data and the spectrum data (i.e., the x-y data), and to generate processed data. The processing module is a software program running on a processor, which is for example embedded in a personal computer (PC), logically connected to the processing circuit, or more generally in a user terminal, e.g. PC, tablet or smartphone. For example, the software in the processing module may include routines, programs, objects, components, and data structures which perform particular functions. In the usual ways, the processing module for spectral analysis is connected to a rendering module having graphic processing for rendering a bidimensional spectrum on a display screen of the user terminal. The user terminal is provided with an input unit (e.g. keyboard, touch screen, etc.), for interaction with the user.

In other embodiments, the processor running the processing module can be housed in the spectroscopic apparatus, which can be provided with a PC access port, e.g. in its housing, for connection with an external computer and/or to a display screen. In a particular embodiment, the processing module is configured to analyse the spectral intensity distribution to determine the presence or absence of a spectral pattern indicative of artificial treatment, to display the spectral intensity distribution and, if the spectral pattern is determined to be present, to provide an indication of the position of the spectral pattern on the displayed spectral intensity distribution. According to this embodiment, establishing that the diamond has been artificially treated is performed by a user viewing the displayed spectrum and a displayed indication of the position of the spectral pattern, for example in the form of one or more lines superimposed on the displayed spectrum.

The method of the embodiment of FIG. 9 comprises, after conversion of the acquired image and, optionally, display of a photoluminescence spectrum, verifying that the analysed gemstone is a diamond by checking for the presence or absence of a peak at a wavelength corresponding to the Raman wavenumber shift of 1332.5 cm$^{-1}$, which identifies the gemstone as diamond.

Verifying the nature of the gemstone is implemented by data processing of the x-y data (indicated with step 45). Verification is performed automatically by the processing module for spectral analysis which is configured to perform data processing comprising analysing the x-y data of the spectrum to determine if the spectral intensity has a value larger than a predetermined threshold intensity value at a wavelength corresponding to the Raman wavenumber shift for a diamond (46). If the intensity has a value larger than the threshold, the verification produces a positive result by determining that the gemstone is a diamond and the process proceeds with the subsequent programmed steps. If the result of the verification is in the negative, the process terminates. Termination of the process is represented in the flow chart by end block 50.

In an embodiment, in the data processing, the software calculates the mean value $I_{RAMAN}$ of the Raman signal in a first wavenumber range comprising the wavenumber value expected for the Raman line, where the intensity has a peak maximum (for example, from 1330 cm$^{-1}$ to 1334 cm$^{-1}$). After calculation of the mean value, data processing comprises dividing this value by the standard deviation $\sigma_A$ of the collected intensity, which is determined in the spectral intensity distribution in a signal-free sub-range of wavenumbers outside the wavenumber values at which the maximum of the Raman signal is expected (for example, from 1310 cm$^{-1}$ to 1320 cm$^{-1}$). Subsequently, if the calculated ratio $I_{RAMAN}/\sigma_A$ is lower than or equal to 2, the outcome is that the sample is not a diamond and the process ends at block 50. Otherwise, namely if $I_{RAMAN}/\sigma_A > 2$, the outcome is that the sample is a diamond and the process goes on.

If the verification gives positive result, the method proceeds with step 49. Preferably, before proceedings, the method comprises providing an output indicating the positive result (47), for example by visualising a message "The sample is a diamond" on a display screen of the user terminal.

If the verification gives negative result, the process terminates as illustrated by block 50. Preferably, the process terminates with a message (48), which can be visualised on the display screen, informing the user that the sample under analysis is not a diamond and that the process ends.

Subsequently to the positive verification that the sample under analysis is a diamond, the method comprises requesting a manual input from the user concerning the diamond colour (step 49). Requesting a manual input can be carried out by either selecting between different options visualised on the display or by typing the colour in a field provided by the application by means of the input unit. In an embodiment, colours accepted as input data are grouped in three colour groups: a first group 51 associated with yellow, orange and brown ("yellow"), a second group 52 associated with blue, green, blue-green and black colours ("blue-green or black"), and a third group 53 associated with the absence of a colour ("colourless").

If input data indicative of the colour of the diamond is categorised in the group 53 "colourless", the process terminates (block 50), because no reliable spectral indicators are observed in the collected wavelength region of wavelengths larger than 600 nm.

Since detection of the GR1 spectral line at 741 nm in the spectrum can reliably detect if a "blue-green or black"

diamond of the second group has been artificially treated, the Applicant has realised that, if the image from the light scattered from the gemstone is acquired across a spectral region comprising the spectral pattern and the GR1 line, the method according to the present embodiment allows the examination of the nature of also "blue-green or black" diamonds.

FIG. 10 is a plot of intensity vs. wavelength for light emission from an artificially irradiated blue diamond, showing the photoluminescence spectra of an artificially irradiated blue diamond. The photoluminescence signal was collected by employing the same analysis apparatus for the spectra of FIG. 4. The photoluminescence intensity exhibits a strong Raman line at 691 nm, corresponding to a wave-number shift of about 1332 cm$^{-1}$ from the incident radiation and identifying the sample as single-crystal diamond. A peak at about 741 nm, which is ascribed to the GR1 optical centre, is clearly visible and intense. Further, a broad band at wavelengths larger than 741 nm, which can be associated with a vibrational side band of the GR1 emission. No spectral indicators at 681, 705 and 725 nm were detected.

In accordance with some embodiments, if input data is categorised in the second group (52), the method comprises determining if the GR1 spectral line at 741 nm is present or absent in the spectrum (54,55). Determination of the presence of the GR1 spectral line is preferably done automatically. In an embodiment, in the data processing 54, the software calculates the mean value $I_{GR1}$ of the photoluminescence signal in the wavelength range comprising the GR1 peak maximum and having as minimum wavelength value larger than 725 nm (for example, from 738 nm to 744 nm) and divides this value by $\sigma_A$. If the calculated ratio $I_{GR1}/\sigma_A$ is lower or equal to 2 then the outcome is that the GR1 peak is absent. If the calculated ratio $I_{GR1}/\sigma_A$ is greater than 2, then the outcome is that the GR1 peak is present.

If the result of determining if the GR1 spectral line at 741 nm is present or absent in the spectrum is positive, the software establishes that the blue-green or black diamond is treated and the method proceed to show the result that the diamond is treated, for example by visualising a label "The diamond is treated" on a display screen of the user terminal. If the result is negative, software establishes that the diamond is untreated and the method proceed to block 56 to show the result that the diamond is untreated, for example by visualising a label "The diamond is untreated" on a display screen of the user terminal.

If the input data is categorised in the group "yellow" (51), the method comprises checking for evidence of artificial treatment by data processing 58. Checking for evidence of artificial treatment of the "yellow" group of diamonds comprises:

analysing the emission spectrum to determine the presence or absence of an intensity peak at 681 nm (59);
if an intensity peak at 681 nm is determined to be present, establishing that the diamond is treated and indicating the result (62). Then, the process terminates (50);
if an intensity peak at 681 nm is determined to be absent, the method proceeds to block 60 by analysing the emission spectrum to determine the presence or absence of an intensity peak at 705 nm;
if an intensity peak at 705 nm is determined to be absent, establishing that the diamond is untreated and indicating the result (63). The process then terminates;
if an intensity peak at 705 nm is determined to be present, the method proceeds by analysing the emission spectrum to determine the presence or absence of an intensity peak at 725 nm (61);
if an intensity peak at 725 nm is determined to be present, establishing that the diamond is treated and the process ends (50) after providing an indication that the diamond is treated (62) as output.
if an intensity peak at 725 nm is determined to be absent, establishing that the diamond is untreated and the process ends (50) after providing an indication that the diamond is untreated (63) as output.

Indication to the user of the result that the analysed gemstone is treated or untreated can be made in conventional ways, for example by visualising a message, such as "Diamond is treated" or "Diamond is untreated" on the display screen of the user terminal (as in the embodiment of FIG. 9). In another embodiment, providing an output indicating the result is made by providing as output a switch-on of a red light (diamond treated) or of a green light (diamond untreated) on the spectroscopic apparatus. In a still further embodiment, providing an output indicating that the diamond has been artificially treated comprising activating a sound signal, wherein activation is triggered by the processing module to produce an audio sound from an audio unit of a user terminal embedding the processing unit or from an electronic alarm unit (per se known) installed on the spectroscopic apparatus and logically connected to the processing module.

An automatic procedure for data processing is preferably implemented for the process starting from block 58, i.e. for checking for evidence of artificial treatment of the "yellow" diamonds. In an embodiment, the processing module for spectral analysis calculates the mean value $I_{681}$ of the photoluminescence signal in the wavelength range comprising the expected value for the peak maximum and having a range upper limit smaller than 700 nm (not to include the second spectral indicator at 705 nm) and preferably smaller than the wavelength of the expected Raman peak. For example, for an excitation wavelength of 633 nm, the Raman peak is at 691 nm and the wavelength range is selected from 676 nm to 686 nm. The calculated mean value is divided by $\sigma_A$, the previously defined standard deviation. If the calculated ratio $I_{681}/\sigma_A$ is lower than or equal to 2, the outcome is that the peak is absent. If the calculated ratio is greater than 2, the outcome is that the peak is present. If the peak is determined to be present, the process ends by indicating the result that the diamond is treated (62).

If the peak at 681 nm is determined to be absent, subsequently to the checking for the occurrence of the peak at 681 nm, the method comprises checking the occurrence of an intensity peak at 705 nm (60). In an embodiment, to carry out the check of the occurrence if the 705 nm-peak, the processor calculates the mean value $I_{705}$ of the photoluminescence signal in the wavelength range comprising the wavelength value at which the peak maximum of the second spectral indicator is expected, wherein the range has a lower limit larger than the wavelength of the first indicator and an upper limit smaller than the wavelength of the third indicator (e.g. from 700 nm to 710 nm). The mean value $I_{705}$ is then divided by $\sigma_A$. If the calculated ratio $I_{705}/\sigma_A$ is lower or equal to 2, the outcome is that the peak is absent, whereas if it is greater than 2, the outcome is that the peak is present. If the checking of a peak at 705 nm gives a negative result, the process ends and the result that the diamond is untreated is indicated to the user (62).

If the checking of a peak at 705 nm gives positive result, the method comprises checking for the occurrence of an intensity peak at 725 nm. In an embodiment, to carry out the check of the occurrence of the 725 nm peak, the processor calculates the mean value Ins of the photoluminescence signal in the wavelength range comprising the wavelength at which the peak maximum is expected, wherein the range is selected to have a lower limit larger than the wavelength of the second spectral indicator, preferably within ±5 nm about the expected value of 725 nm, (e.g. from 720 nm to 730 nm). The mean value $I_{725}$ is divided this value by $\sigma_A$. If the calculated ratio $I_{725}/\sigma_A$ is lower or equal to 2, the outcome is that the peak is absent and the process establishes that the sample is untreated. If the calculated ratio is greater than 2 then the outcome is that the peak is present and the process establishes that the sample is treated. In either case, the process terminated after having provided an output indicating that the sample is treated or untreated (62 or 63)

As exemplified by the embodiment of FIG. 9, although the presently disclosed method is particularly suitable to discriminate diamonds with natural coloration from artificially coloured diamonds, the method can also be used to discriminate diamonds from similar gemstones not composed by diamond phase, such as moissanite, cubic zirconia, and other gemstones with different chemical composition and/or crystal structure. In the embodiment described with reference to the flow chart of FIG. 9, is performed through the detection of the scattered light related to the Raman mode of diamond. Without wishing to be bound by theory, the light diffused by Raman effect at a wavelength shifted from the incident wavelength is dependent on the crystal symmetry, the bond length values, and the mass of the involved atoms, and is therefore an identifier of the diamond composition or crystallographic structure. According to some embodiments, excitation wavelength of the primary beam is selected so as to have the Raman mode falling within the wavelength range comprising the spectral pattern, preferably between 670 nm to 750 nm. Preferably, the excitation wavelength is of from 600 to 675 nm.

In some other embodiments, verification of the presence of the Raman peak can be done manually by a user who, by observing the displayed spectrum, enters the result of the check. To this purpose, a template can be graphically rendered on the display with fields to be selected or filled in.

Some further embodiments do not comprise the verification that the gemstone is a diamond. In such embodiments, the identification of the gemstone can be carried out by other tests or by visual examination of an expert.

FIG. 11 is a flow chart of a method of detection of artificially generated colour in a diamond, in accordance with another embodiment consistent with the present disclosure. The sample analysed in this embodiment is a yellow coloured diamond. First steps 41 to 44 of the method of FIG. 11 correspond to the steps indicated with the same referral number of FIG. 9. After conversion of the acquired image (43) and, optionally, after visualization of the intensity distribution (44), the x-y data are entered in a processing module for implementing the spectral analysis. The processing module is configured to perform data processing on the x-y data as spectral intensity distribution (71). The automatic procedure for determining whether the yellow diamond has been artificially treated to change its colour comprises:

analysing the spectral intensity distribution to determine the presence or absence of an intensity peak at 681 nm (72);

if an intensity peak at 681 nm is determined to be present, establishing that the diamond is treated (to 76);

if an intensity peak at 681 nm is determined to be absent, the method proceeds to block 73 by analysing the spectral intensity distribution to determine the presence or absence of an intensity peak at 705 nm;

if an intensity peak at 705 nm is determined to be absent, establishing that the diamond is untreated (to 77);

if an intensity peak at 705 nm is determined to be present, the method proceeds by analysing the spectral intensity distribution to determine the presence or absence of an intensity peak at 725 nm (74);

if an intensity peak at 725 nm are determined to be present, establishing that the diamond is treated (to 76).

if an intensity peak at 725 nm are determined to be absent, establishing that the diamond is untreated and the process ends (50).

After establishing that the diamond is treated or untreated (76, 77), the method comprises providing an output indicating that the diamond is treated or untreated, respectively (75, 78).

After indication of the natural or artificial origin of the diamond (75, 76), the process terminates at block 79.

In the procedure of FIG. 11, indication to the user of the result that the yellow diamond is treated or untreated is made by visualising a message, such as "Diamond is treated" or "Diamond is untreated" on the display screen of a user terminal embedding the processing module or being logically connected to the processing module. In another embodiment, providing an output indicating the result is made by providing as output a switch-on of a red light if the diamond is treated on the spectroscopic apparatus. In a still further embodiment, providing an output indicating that the diamond has been artificially treated comprising activating a sound signal, wherein activation is triggered by the processing module to produce an audio sound from an audio unit of a user terminal embedding the processing unit or from an electronic alarm unit (per se known) installed on the spectroscopic apparatus and logically connected to the processing module.

FIG. 12 is a flow chart of a method of spectroscopic analysis of a gemstone, in accordance with another embodiment consistent with the present disclosure. This method can be applied for the analysis of a "yellow" coloured diamond-like gemstone to verify that the gemstone is a diamond (and, for example, not a cubic zirconia) and, if the verification has positive result, to check whether the diamond has undergone artificial treatments. Initial steps 41 to 47 correspond to data processing operations indicated with same referral numbers in FIG. 9. Subsequently to the positive verification that the sample under analysis is a diamond and the provision of an output to the user of the result (47), the method proceeds by checking for evidence of an artificial treatment on the diamond.

The processing module is configured to perform data processing on the x-y data as spectral intensity distribution (81). The automatic procedure for determining whether the diamond has been artificially treated to change its colour comprises:

analysing the spectral intensity distribution to determine the presence or absence of an intensity peak at 681 nm (82);

if an intensity peak at 681 nm is determined to be present, establishing that the diamond is treated (to 84);

if an intensity peak at 681 nm is determined to be absent, the method proceeds to block 83 by analysing the spectral intensity distribution to determine the presence or absence of an intensity peak at 705 nm;

if an intensity peak at 705 nm is determined to be absent, establishing that the diamond is untreated (to 85);

if an intensity peak at 705 nm is determined to be present, the method proceeds by analysing the spectral intensity distribution to determine the presence or absence of an intensity peak at 725 nm (86);

if an intensity peak at 725 nm is determined to be present, establishing that the diamond is treated (to 84), and if an intensity peak at 725 nm is determined to be absent, establishing that the diamond is untreated.

After establishing that the diamond is treated or untreated (to 84 or 85), the method comprises providing an output indicating that the diamond is treated or untreated, respectively (88,87)

After providing an output indicating the natural or artificial origin of the diamond colour (88, 87), the process terminates at block 89.

As exemplified in the foregoing description, analysis for artificial treatment can be based on a simple yes-no method with a very low level of uncertainty.

In accordance with some embodiments, the outcome of the analysis is not constrained by or based on the particular shape, or cut, or surface condition of the analysed gemstone. In some embodiments, the method is also applicable for verifying that the analysed gemstone belongs to the diamond crystallographic species through the detection of the characteristic Raman mode of diamond, by means of a spectroscopic device that can be simple and inexpensive.

In some embodiments, spectroscopic apparatus for verifying whether a gem is a diamond can be advantageously used for black diamonds, which are particularly difficult to check by means of usual gemmological inspection carried out by using basic instrumentation, such as refractometer, hydrostatic balance, microscope or Wood lamp. Because of the variability of black diamond properties, such as the density value, the analysis of this gem generally requires the ability of skilled analysts. In addition, the high refractive index of black diamond may not allow the use of a standard refractometer, whereas its poor transparency makes it hard to identify a diamond by using a gemmological microscope. For these reasons, a spectroscopic apparatus is often necessary for the identification of the nature of a black gem.

EXAMPLE

An apparatus of the type described with reference to FIGS. 1a and 1b was used for the detection of stimulated photoluminescence spectra of FIG. 4. A light beam from a laser at 633 nm was focussed on a diamond to generate optically-excited stimulated emission collected by a first focussing lens 17, which was a plain-convex lens placed at focal length from the sample (e.g. 40.0 mm). Stimulated emission produced a divergent light beam emerging from the sample. A first focussing lens 17 converted the divergent beam in a collimated beam, which was then directed to a second focussing lens, which was a plain-convex lens, with focal length of 25.0 mm, to focalize the collimated beam onto slit 19. The first two lenses formed the first focussing optical system of this example. From the slit the secondary beam emerged as a divergent beam. At the downstream side of slit 19 with respect to the sample, a wavelength-selective filter 20 produced a spectrally selected light beam. The filter optical properties depend on the power and on the type of the light source. In the present example, filter 20 was a high-pass filter with cut-off wavelength of 650 nm. A collimating lens 21 with focal length of 35.0 mm collimated the divergent beam from the slit on a reflection diffraction grating 22.

Selection of a suitable width of the slit mainly depends on the dispersing power of the reflection diffraction grating and on the size of the photodetector device. In the present example, the reflection diffraction grating had a groove density of 1200 grooves/mm and a slit with width of from 0.1 to 0.5 mm was selected to obtain a spectral resolution, i.e. the ability to separate between two adjacent spectral lines ($\Delta\lambda$), of 0.5-1.0 nm. By choosing an appropriate angle of incidence of the beam on the grating system, the produced dispersed beam impinging on the detector area lies within the spectral region of interest, in the present example of from 650 to 800 nm. In some embodiments, a relatively high dispersion, for example larger than 2 mrad/nm, can be advantageous since it helps increasing compactness of the spectroscopic apparatus.

The spectrally dispersed beam was collected and focalized by a focussing lens 23 of focal length of 35.0 mm. The photodetector device was placed at the focal plane of lens 23.

The photodetector device was a CCD sensor of suitable finite size, for example with size of from $3.25 \times 2.45$ mm$^2$ to $6.5 \times 4.9$ mm$^2$, to allow the collection of a spectral region of approximate width of from 100 nm to 200 nm, respectively—assuming a linear relation between spectral distribution and number of pixel—with a spectral resolution of 0.5-1.0 nm.

All optical components of the apparatus of the present example were fixed, i.e. not movable for tuning of optical properties, and no additional alignment of the components was necessary before or during the analysis.

A relatively short optical path of the emitted beam can be obtained by selecting optical components so as to make possible for the components to be mounted on an optical bench to be contained in a portable case with size of the order of few tens of centimetres.

The spectroscopic analysis apparatus in accordance with the present example can be constructed as a hand-held apparatus of relatively low cost.

The invention claimed is:

1. A method of spectroscopic analysis of a yellow diamond gemstone for determining whether the diamond has been artificially treated to change its colour, the method comprising:

generating light emission from a diamond upon optical excitation at an excitation wavelength from 600 nanometers (nm) to 675 nm, wherein the diamond is exposed at room temperature to a light beam that generates optically excited emission and scattered light;

optically producing a dispersed light emission;

detecting the dispersed light emission across a collected spectral region by means of a photodetector device to electrically generate output signals, wherein the collected spectral region comprises emission wavelengths of from 670 nm to 750 nm;

processing the output signals to produce a spectral intensity distribution as a function of emission wavelengths;

analysing the spectral intensity distribution to determine the presence or absence of a spectral pattern comprising either an intensity peak at 681 nm or a combination of intensity peaks at respective wavelengths 705 nm and 725 nm;

if, as a result of analysing, a spectral pattern is determined to be present, establishing that the diamond has been artificially treated to change its colour; and if, as a result of analysing, a spectral pattern is determined to be absent, establishing that the diamond has not been treated to change its colour.

2. The method of claim 1, wherein the spectral pattern is at least one spectral feature selected from the group consisting of an intensity peak at 681 nm, two intensity peaks positioned at the respective wavelengths of 705 nm and at 725 nm, and three intensity peaks positioned at respective wavelengths of 681 nm, 705 nm and 725 nm.

3. The method of claim 1, further comprising:
after establishing that the diamond has been artificially treated, providing an output indicating that the diamond has been artificially treated.

4. The method of claim 1, wherein analysing the spectral intensity distribution and establishing that the diamond is treated or untreated is performed automatically.

5. The method of claim 1, further comprising:
after analysing the spectral intensity distribution and before establishing if the diamond is untreated or has been artificially treated, visualising on a display screen the spectral intensity distribution.

6. The method of claim 1, wherein generating light emission from a diamond comprises:
irradiating a diamond with a primary optical beam at an excitation wavelength to generate excited light emission in the form of a secondary optical beam.

7. The method of claim 6, wherein optically producing a dispersed light emission comprises:
focussing the secondary optical beam onto a slit to produce an image of light emission, and
spectrally dispersing the secondary light beam to spatially separate the light emission imaged by the slit into wavelengths across an emission wavelength region.

8. The method of claim 1, wherein analysing the spectral intensity distribution to determine the presence or absence of a spectral pattern comprises:
analysing the spectral intensity distribution to determine the presence or absence of an intensity peak at 681 nm;
if, as a result of analysing, an intensity peak at 681 nm is determined to be present, determining that the spectral pattern is present;
if, as a result of analysing, an intensity peak at 681 nm is determined to be absent, analysing the spectral intensity distribution to determine the presence or absence of an intensity peak at 705 nm;
if, as a result of analysing, an intensity peak at 705 nm is determined to be absent, determining that the spectral pattern is absent;
if an intensity peak at 705 nm is determined to be present, analysing the spectral intensity distribution to determine the presence or absence of an intensity peak at 725 nm;
if an intensity peak at 725 nm is determined to be present, determining that the spectral pattern is present,
if an intensity peak at 725 nm is determined to be absent, determining that the spectral pattern is absent.

9. The method of claim 1, wherein the yellow diamond gemstone is a yellow diamond natural gemstone.

10. A method of identifying a gemstone as a yellow diamond and, if the gemstone is identified as diamond, of determining whether the diamond has been artificially treated, the method comprising:
generating light emission from a diamond at room temperature upon optical excitation at an excitation wavelength from 600 nanometers (nm) to 675 nm;
optically producing a dispersed light emission;
detecting the dispersed light emission across a collected spectral region by means of a photodetector device to electrically generate output signals, wherein the collected spectral region comprises emission wavelengths of from 670 nm to 750 nm;
processing the output signals to produce a spectral intensity distribution as a function of emission wavelengths;
analysing the spectral intensity distribution to determine the presence or absence of a Raman peak at a wavelength corresponding to a wavenumber shift between the excitation wavelength and the scattered wavelength of 1332.5 cm$^{-1}$;
if, as a result of analysing, a Raman peak is determined to be absent, establishing that the gemstone is not a diamond and providing an output indicating that the gemstone is not a diamond;
if, as a result of analysing, a Raman peak is determined to be present, establishing that the gemstone is a diamond and proceed by analysing the spectral intensity distribution to determine the presence or absence of a spectral pattern comprising either an intensity peak at 681 nm or the combination of intensity peaks at respective wavelengths 705 nm and 725 nm;
if, as a result of analysing, a spectral pattern is determined to be present, establishing that the diamond has been artificially treated to change its colour;
if, as a result of analysing, a spectral pattern is determined to be absent, establishing that the diamond has not been treated to change its colour; and
providing an output indicating that the diamond has been artificially treated.

11. The method of claim 10, wherein the yellow diamond gemstone is a yellow diamond natural gemstone.

12. The method of claim 1, further comprising:
before analysing the spectral intensity distribution to determine the presence or absence of a spectral pattern, selecting a diamond colour from two colour groups: a first colour group of yellow, orange, and brown and a second colour group of blue-green or black;
if the diamond colour is selected to be the first group of colour, proceeding with analysing the spectral intensity distribution to determine the presence or absence of the spectral pattern and establishing if the diamond has been artificially treated;
if the diamond colour is selected to be the second group of colour, analysing the spectral intensity distribution to determine the presence or absence of a GR1 spectral feature at 741 nm;
if, as a result of analysing, a GR1 spectral feature is determined to be present, establishing that the diamond in the second colour group has been artificially treated to change its colour and providing an output that the diamond has been artificially treated; and
if, as a result of analysing, a GR1 spectral feature is determined to be absent, establishing that the diamond has not been treated to change its colour.

13. A spectroscopic apparatus, comprising:
a source emitting a primary beam at an excitation wavelength from 600 nanometers (nm) to 675 nm to be directed onto a yellow diamond gemstone to generate light emission from the diamond, wherein the diamond is exposed at room temperature to the primary beam;
a first optical focussing system arranged to focus the light emission onto a slit to produce an image of light emission;
a spectrally dispersing device arranged to spatially separate the light emission imaged by the slit into wavelengths, the spectrally dispersing device being configured to produce a spatially dispersed light emission;
a photodetector device arranged to collect the dispersed light emission across a collected spectral region and to electrically generate output signals, wherein the collected spectral region comprises a wavelength region of from 670 nm to 750 nm;

a processing circuit configured to receive the output signals and to process them to produce a spectral intensity distribution as a function of emission wavelength across the collected wavelength region, and a processor operatively connected to the processing circuit comprising a processing module configured to:

analyse the spectral intensity distribution to determine the presence or absence of a spectral pattern comprising either an intensity peak at 681 nm or the combination of intensity peaks at respective wavelengths 705 nm and 725 nm;

establish that the diamond has been artificially treated to change its colour if, as a result of analysing, a spectral pattern is determined to be present, and establish that the diamond has not been treated to change its colour if, as a result of analysing, a spectral pattern is determined to be absent.

14. The apparatus of claim 13, wherein the processor comprises a rendering module operatively connected to the processing module for rendering a graph of the spectral intensity distribution on a display screen operatively connected to the processor.

15. The apparatus of claim 13, wherein the processing module is further configured to trigger the provision of an output indicating that the diamond has been artificially treated, after establishing that the diamond has been artificially treated.

16. The apparatus of claim 13, wherein the spectrally dispersing device is a reflection diffraction grating or a transmission diffraction grating.

17. The apparatus of claim 13, further comprising:

a second optical focussing system arranged to collect the dispersed light emission from the spectrally dispersing device and to direct a focussed dispersed light emission onto the photodetector device.

18. The method of claim 2, further comprising:

after establishing that the diamond has been artificially treated, providing an output indicating that the diamond has been artificially treated.

19. The method of claim 10, further comprising:

before analysing the spectral intensity distribution to determine the presence or absence of a spectral pattern, selecting a diamond colour from two colour groups: a first colour group of yellow, orange, and brown and a second colour group of blue-green or black;

if the diamond colour is selected to be the first group of colour, proceeding with analysing the spectral intensity distribution to determine the presence or absence of the spectral pattern and establishing if the diamond has been artificially treated;

if the diamond colour is selected to be the second group of colour, analysing the spectral intensity distribution to determine the presence or absence of a GR1 spectral feature at 741 nm;

if, as a result of analysing, a GR1 spectral feature is determined to be present, establishing that the diamond in the second colour group has been artificially treated to change its colour and providing an output that the diamond has been artificially treated; and if, as a result of analysing, a GR1 spectral feature is determined to be absent, establishing that the diamond has not been treated to change its colour.

20. The apparatus of claim 14, wherein the processing module is further configured to trigger the provision of an output indicating that the diamond has been artificially treated, after establishing that the diamond has been artificially treated.

* * * * *